US006903068B1

(12) United States Patent
Stanton et al.

(10) Patent No.: US 6,903,068 B1
(45) Date of Patent: *Jun. 7, 2005

(54) USE OF COLOSTRININ, CONSTITUENT PEPTIDES THEREOF, AND ANALOGS THEREOF FOR INDUCING CYTOKINES

(75) Inventors: G. John Stanton, Texas City, TX (US); Thomas K. Hughes, Jr., Galveston, TX (US); Istvan Boldogh, Galveston, TX (US); Jerzy A. Georgiades, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 488 days.

This patent is subject to a terminal disclaimer.

(21) Appl. No.: 09/641,801

(22) Filed: Aug. 17, 2000

Related U.S. Application Data

(60) Continuation-in-part of application No. 10/281,652, filed on Oct. 28, 2002, which is a division of application No. 09/641,803, filed on Aug. 17, 2000, now Pat. No. 6,500,798.
(60) Provisional application No. 60/420,369, filed on Oct. 22, 2002, and provisional application No. 60/149,311, filed on Aug. 17, 1999.

(51) Int. Cl.[7] .................. A61K 38/00; A61K 38/02; A61K 38/08; A61K 38/18
(52) U.S. Cl. .................. 514/2; 514/12; 514/13; 514/14; 514/15; 514/16; 514/17; 530/300; 530/324; 530/326; 530/327; 530/328; 530/329
(58) Field of Search .................. 514/2, 12, 13, 514/14, 15, 16, 17, 18; 530/300, 324, 326, 327, 328, 329, 350, 334; 424/85.1, 535

(56) References Cited

U.S. PATENT DOCUMENTS

| | | | |
|---|---|---|---|
| 4,938,949 A | | 7/1990 | Borch et al. |
| 5,595,887 A | | 1/1997 | Coolidge et al. |
| 6,040,180 A | | 3/2000 | Johe |
| 6,410,058 B2 | * | 6/2002 | Gohlke et al. .............. 424/535 |
| 6,500,798 B1 | * | 12/2002 | Stanton et al. .................. 514/2 |
| 2003/0091606 A1 | | 5/2003 | Stanton et al. |

FOREIGN PATENT DOCUMENTS

| | | | |
|---|---|---|---|
| JP | 06 041191 A | | 2/1994 |
| WO | WO 95/00155 | | 1/1995 |
| WO | WO 95/30686 | | 11/1995 |
| WO | WO 98/14473 | * | 4/1998 |
| WO | WO 99/65329 | | 12/1999 |
| WO | WO 00/75173 | | 12/2000 |
| WO | WO 01/11937 | | 2/2001 |
| WO | WO 01/12650 | | 2/2001 |
| WO | WO 01/12651 | | 2/2001 |
| WO | WO 02/13849 | | 2/2002 |
| WO | WO 02/13850 | | 2/2002 |
| WO | WO 02/13851 | | 2/2002 |
| WO | WO 03/33423 | | 10/2003 |

OTHER PUBLICATIONS

Kruzel et al. (Dec. 2001) "Towards an Understanding of Biological Role of Colonstrinin Peptides." Journal of Molecular Neuroscience 17(3): 379–389.*

Inglot, Junsz, and Lisowski Colostrinine:a Proline–Rich Polypeptide from Ovine Colostrum Is a Modest Cytokine Inducer in Human Leukocytes, 1996, Archivum Immunologiae et Therapiae Experimentalis (44) 215–224.*

Elgert, "Immunology: Understanding the Immune System" Text (1996) Wiley–Liss 1st Ed. pp. 24–26 and 199–217.*

Ngo et al. Computational Complexity, Protein Structure Prediction, and the Levinthal Paradox (1994) The Protein Folding Problem and Teriary Structure Prediction (#14), 491–495.*

Wells Addivity of Mutational Effects in Proteins (1990) Biochemistry (29): 37, 8509–8517.*

Babbit, ed., *The Vanderbilt Rubber Handbook*, R.T. Vanderbilt Company, Inc., Norwalk, CT, pp. 344–397 (1978).

Bespalov et al., "Fabs specific for 8–oxoguanine: control of DNA binding," *J Mol Biol.* Nov. 12, 1999;293(5):1085–95.

Blach–Olszewska et al., "Stimulatory effect of ovine colostrinine (a proline–rich polypeptide) on interferons and tumor necrosis factor production by murine resident peritoneal cells," *Arch Immunol Ther Exp (Warsz).* 1997; 45(1):43–7.

Buescher et al., "Clostral antioxidants: separation and characterization of two activities in human colostrum," *J Pediatr Gastroenterol Nutr*1. Jan. 1992; 14(1):47–56.

Calingasan et al., "Protein–bound acrolein: a novel marker of oxidative stress in Alzheimer's disease," *J. Neurochem.* Feb. 1999;72(2):751–6.

Chao "Growth factor signaling: where is the specificity?" *Cell.* Mar. 20, 1992; 68(6):995–7.

Esterbauer et al., "Chemistry and biochemistry of 4–hydroxynonenal, malonaldehyde and related aldehydes," *Free Radic Biol Med.* 1991;11(1):81–128.

Fields et al., *Synthetic Peptides: A User's Guide*, W.M. Freeman & Company, New York, NY, pp. 77–183 (1992).

Fillmore et al., "Differentiation of PC12 cells with nerve growth factor is associated with induction of transin synthesis and release," *J Neurosci Res.* Apr. 1992;31(4):662–9.

Gabbita et al., "Increased nuclear DNA oxidation in the brain in Alzheimer's disease," *J Neurochem.* Nov. 1998;71(5):2034–40.

Gabbita et al., "Decrease in peptide methionine sulfoxide reductase in Alzheimer's disease brain," *J Neurochem.* Oct. 1999;73(4):1660–6.

(Continued)

Primary Examiner—Elizabeth C. Kemmerer
Assistant Examiner—Christopher James Nichols
(74) Attorney, Agent, or Firm—Mueting, Raasch & Gebhardt, P.A.

(57) ABSTRACT

The present invention discloses a use of colostrinin, a constituent peptide thereof, and/or an analog thereof as an immunological regulator and as a blood cell regulator in animals including humans.

37 Claims, 9 Drawing Sheets

OTHER PUBLICATIONS

Good et al., "Evidence of neuronal oxidative damage in Alzheimer's disease," *Am J Pathol.* Jul. 1996;149(1):21–8.

Gratama et al., "Flow cytometric quantitation of immunofluorescence intensity: problems and perspectives. European Working Group on Clinical Cell Analysis," *Cytometry,* Oct. 1, 1998;33(2):166–78.

Grunwald et al., "In situ analysis of chromatin proteins during development and cell differentiation using flow cytometry," *Methods Mol Biol.* 1999;119:443–54.

Hensley et al., "Brain regional correspondence between Alzheimer's disease histopathology and biomarkers of protein oxidation," *J Neurochem.* Nov. 1995; 65(5):2146–56.

Hughes et al., "Modulation of immune responses by anabolic androgenic steroids," *Int J Immunopharmacol.* Nov. 1995;17(11):857–63.

Inglot et al., "Colostrinine: a proline–rich polypeptide from ovine colostrum is a modest cytokine inducer in human leukocytes," *Arch Immunol Ther Exp (Warsz).* 1996;44(4):215–24.

Inglot et al., "Colostrinin for treatment of Alzheimer's disease," *European Cytokine Network.* Sep. 1996;7(3):458(abstract 51).

Inglot et al., "Tumor–associated antigens are cytokine inducers and hyporeactivity factors to the immune system," *Biotherapy.* 1998;11(1):27–37.

Janusz et al., "Isolation and characterization of a proline–rich polypeptide from ovine colostrum," *FEBS Lett.* Dec. 15, 1974;49(2):276–9.

Janusz et al., "Chemical and physical characterization of a proline–rich polypeptide from sheep colostrum," *Biochem J.* Oct. 1, 1981;199(1):9–15.

Janusz et al., "Proline–rich polypeptide (PRP)—an immunomodulatory peptide from ovine colostrum," *Arch Immunol Ther Exp (Warsz).* 1993;41(5–6):275–9.

Kim et al., "Simultaneous differentiation and quantitation of erythroblasts and white blood cells on a high throughput clinical haematology analyser," *Clin Lab Haematol.* Feb. 1998;20(1):21–9.

Kooy et al., "Oxidation of 2',7'–dichlorofluorescin by peroxynitrite," *Free Radic Res.* Sep. 1997;27(3):245–54.

LeBel et al., "Evaluation of the probe 2',7'–dichlorofluorescin as an indicator of reactive oxygen species formation and oxidative stress," *Chem Res Toxicol.* Mar.–Apr. 1992;5(2):227–31.

Leszek et al., "Colostrinin: a proline–rich polypeptide (PRP) complex isolated from ovine colostrum for treatment of Alzheimer's disease. A double–blind, placebo–controlled study," *Arch Immunol Ther Exp (Warsz).* 1999;47(6):377–85.

Levi et al., "The mode of action of nerve growth factor in PC12 cells," *Mol Neurobiol.* 1988 Fall;2(3):201–26.

Lovell et al., "Elevated thiobarbituric acid–reactive substances and antioxidant enzyme activity in the brain in Alzheimer's disease," *Neurology.* Aug. 1995; 45(8):1594–601.

Lovell et al., "Elevated 4–hydroxynonenal in ventricular fluid in Alzheimer's disease," *Neurobiol Aging.* Sep.–Oct. 1997;18(5):457–61.

Lovell et al., "Decreased glutathione transferase activity in brain and ventricular fluid in Alzheimer's disease," *Neurology.* Dec. 1998;51(6):1562–6.

Lovell et al., "Increased DNA oxidation and decreased levels of repair products in Alzheimer's disease ventricular CSF," *J Neurochem.* Feb. 1999;72(2):771–6.

Lovell et al., "Decreased base excision repair and increased helicase activity in Alzheimer's disease brain," *Brain Res.* Feb. 7, 2000;855(1):116–23.

Markesberry, "Oxidative stress hypothesis in Alzheimer's disease," *Free Radic Biol Med.* 1997;23(1):134–47.

Markesbery et al., "Four–hydroxynonenal, a product of lipid peroxidation, is increased in the brain in Alzheimer's disease," *Neurobiol Aging.* Jan.–Feb. 1998;19(1):33–6.

Markesbery et al. "Oxidative alterations in Alzheimer's disease," *Brain Pathol.* Jan. 1999;9(1):133–46.

Marshall et al., "Specificity of receptor tyrosine kinase signaling: transient versus sustained extracellular signal–regulated kinase activation," *Cell.* Jan. 1995 27:80(2):179–85.

McHeyzer–Williams et al., "Enumeration and characterization of memory cells in the TH compartment," *Immunol Rev.* Apr. 1996;150:5–21.

Mecocci et al., "Oxidative damage to mitochondrial DNA is Alzheimer's disease," *Ann Neurol.* Nov. 1994;36(5):747–51.

Mishell et al., *Selected Methods in Cellular Immunology,* W.H. Freeman, San Francisco, CA; title page and table of contents only, 9 pages (1980).

Montine et al., "Cerebrospinal fluid F2–isoprostane levels are increased in Alzheimer's disease," *Ann Neurol.* Sep. 1998;44(3):410–3.

Ostrea et al., "Influence of breast–feeding on the restoration of the low serum concentration of vitamin E and beta–carotene in the newborn infant," *Am J Obstet Gynecol.* May 1986;154(5):1014–7.

Peunova et al., "Nitric oxide triggers a switch to growth arrest during differentiation of neuronal cells," *Nature.* May 4, 1995;375(6526):68–73.

Piasecki et al., "Coincidence between spontaneous release of interferon and tumor necrosis factor by colostral leukocytes and the production of a colostrinine by human mammary gland after normal delivery," *Arch Immunol Ther Exp (Warsz),* 1997;45(1):109–17.

Popik et al., "Colostrinin, a polypeptide isolated from early milk, facilitates learning and memory in rats," *Pharmacol Biochem Behav.* Sep. 1999;64(1):183–9.

Prasad et al., "Regional membrane phospholipid alterations in Alzheimer's disease," *Neurochem Res.* Jan. 1998;23(1)81–8.

Roberts II et al., "Formation of isoprostane–like compounds (neuroprostanes) in vivo from docosahexaenoic acid," *J Biol Chem.* May 29, 1998;273(22):13605–12.

Rothe et al., "Flow cytometric analysis of respiratory burst activity in phagocytes with hydroethidine and 2',7'–dichlorofluorescin," *J Leukoc Biol.* May 1990; 47(5):440–8.

Royall et al., "Evaluation of 2',7'–dichlorofluorescin and dihydrorhodamine 123 as fluorescent probes for intracellular H2O2 in cultured endothelial cells," *Arch Biochem Biophys.* May 1993;302(2):348–55.

Subbarao et al., "Autopsy samples of Alzheimer's cortex show increased peroxidation in vitro," *J Neurochem.* Jul. 1990;55(1):342–5.

Schater et al., "Differential susceptibility of plasma proteins to oxidative modification: examination by western blot immunoassay," *Free Radic Biol Med.* Nov, 1994;17(5):429–37.

Singh et al., "Dietary intake, plasma levels of antioxidant vitamins, and oxidative stress in relation to coronary artery disease in elderly subjects," *Am J Cardiol.* Dec. 15, 1995;76(17):1233–8.

Smith et al., "Advanced Maillard reaction end products are associated with Alzheimer disease pathology," *Proc Natl Acad Sci U S A.* Jun. 7, 1994; 91(12):5710–4.

Smith et al., "Oxidative damage in Alzheimer's ," *Nature.* Jul. 11, 1996; 382(6587):120–1.

Smith et al., "Excess brain protein oxidation and enzyme dysfunction in normal aging and in Alzheimer's disease," *Proc Natl Acad Sci U S A.* Dec. 1, 1991; 88(23):10540–3.

Svennerholm et al., Membrane lipids, selectively diminished in Alzheimer brains, suggest synapse loss as a primary event in early–onset form (type I) and demyelination in late–onset form (type II), *J Neurochem.* Mar. 1994; 62(3):1039–47.

Takahashi et al., "Spontaneous transformation and immortalization of human endothelial cells," *In Vitro Cell Dev Biol.* Mar. 1990;26(3 Pt 1):265–74.

Tsuchiya et al., "In vivo visualization of oxygen radical–dependent photoemission," *Methods Enzymol (Oxygen Radicals in Biological Systems).* 1994;233C:128–40.

Villas et al., "Flow cytometry: an overview," *Cell Vis.* Jan.–Feb. 1998;5(1):56–61.

Yan et al., "Glycated tau protein in Alzheimer disease: a mechanism for induction of oxidant stress," *Proc Natl Acad Sci U S A.* Aug. 2, 1994;91(16):7787–91.

Zimecki et al., "Effect of a proline–rich polypeptide (PRP) on the development of hemolytic anemia and survival of New Zealand black (NZB) mice," *Arch Immunol Ther Exp (Warsz).* 1991;39(5–6):461–7.

Altin et al., "Differential Induction of Primary–response (TIS) Genes in PC12 Pheochromocytoma Cells and the Unresponsive Variant PC12nnr5," *Journal of Biological Chemistry,* Mar. 25, 1991;266(9): 5410–5406.

Anneren et al., "GTK, a Src–related Tyrosine Kinase, Induces Nerve Growth Factor–independent Neurite Outgrowth in PC 12 Cells through Activation of the Rap1 Pathway," *Journal of Biological Chemistry,* Sep. 15, 2000;275(37): 29153–29161.

Bagchi et al., "Comparative in vitro and in vivo protein kinase C activation by selected pesticides and transition metal salts," *Toxicology Letters,* 1997;91: 31–37.

Bikfalvi et al., "Biological Roles of Fibroblast Growth Factor–2," *Endocrine Reviews,* Feb. 1997;18(1):26–45.

Chen et al., "Lithium Increase Tyrosine Hydroxylase Levels both In Vivo and In Vitro," *Journal of Neurochemistry,* 1998:70(4): 1768–1771.

Cui et al., "Effect of Nucleoside Analogs on Neurite Regeneration and Mitochondrial DNA Synthesis in PC–12 Cells," *Journal of Pharmacology and Experimental Therapeutics,* 1997;280(3): 1228–1234.

Dagø et al., "NS 1231, a novel compound with neurotrophic–like effects in vitro and in vivo," *Journal of Neurochemistry,* 2002;81: 17–24.

DeJongh et al., "Estimation of Systemic Toxicity of Acrylamide by Integration of in vitro Toxicity Data with Kinetic Simulations," *Toxicology and Applied Pharmacology,* 1999;158: 261–268.

Doye et al., "Phosphorylation of Stathmin and Other Proteins Related to Nerve Growth Factor–induced Regulation of PC12 Cells," *Journal of Biological Chemistry,* Jul. 15, 1990;265(20): 11650–11655.

Feng et al., "NF–κB/Rel Proteins are Required for Neuronal Differentiation of SH–SY5Y Neuroblastoma Cells," *Journal of Biological Chemistry,* Oct. 22, 1999;274(43): 30341–30344.

Kandel et al., "Principles of Neural Science," 4$^{th}$ Ed.; 2002: 67–81, 85–86.

Kim et al., "Insulin–like Growth Factor–I–mediated Neurite Outgrowth in Vitro Requires Mitogen–activated Protein Kinase Activation," *Journal of Biological Chemistry,* Aug. 22, 1997;272(34): 21268–21273.

Kim et al., "Differential Regulation of Insulin Receptor Substrate–2 and Mitogen–Activated Protein Kinase Tyrosine Phosphorylation by Phosphatidylinositol 3–Kinase Inhibitors in SH–SY5Y Human Neuroblastoma Cells," *Endocrinology,* 1998;139(12): 4881–4889.

Lachyankar et al., "A Role for Nuclear PTEN in Neuronal Differentiation," *Journal of Neuroscience,* Feb. 15, 2000;20(4): 1404–1413.

Ley et al., "Adhesion Molecules in Lymphocyte Trafficking and Colitis," *Gastroenterology,* Oct. 2001;121(4):Editorial: 1008–1010.

Noble et al., "Overexpression of Dynamin is Induced by Chronic Stimulation of μ– but Not δ–Opioid Receptors: Relationships with μ–Related Morphine Dependence," *Molecular Pharmcology,* 2000;58: 159–166.

Ponthan et al., "The Synthetic Retinoid RO 13–6307 induces Neuroblastoma Differentiation in vitro and inhibits Neuroblastoma Tumour growth in vivo," *Int. J. Cancer,* 2003:104: 418–424.

Popik et al., "Cognitive effects of Colostral–Val nonapeptide in aged rats," *Behavioral Brain Research,* Jan. 29, 2001;118(2): 201–208.

Puglianiello et al., "IGF–I stimulates chemotasix of human neuroblasts. Involvement of type 1 IGF receptor, IGF binding proteins, phosphatidylinositol–3 kinase pathway and plasmin system," *Journal of Endocrinology,* 2000;165: 123–131.

Salmi et al., "Immune Cell Trafficking in Uterus and Early Life is Dominated by the Mucosal Addressin MadCAM–1 in Humans," *Gastroenterology,* Oct. 2001;121(4): 853–864.

Xiang–Ming et al., "Gating kinetics of potassium channel and effects of nerve growth factors in PC12 cells analyzed with fractal model," *Acta Pharmacol Sin,* Feb. 2001;22(2): 103–110.

Zhen et al., "Lithium regulates protein tyrosine phosphatase activity in vitro and in vivo," *Psychopharmacology,* 2002;162: 379–384.

Cosgaya et al., "Neuronal differentiation of PC12 cells induced by engrailed homeodomain is DNA–binding specific and independent of MAP kinases," *Journal of Cell Science,* 1998;111:2377–2384.

Vaudry et al., "Signaling Pathways for PC12 Cell Differentiation: Making the Right Connections," *Science,* May 31, 2002;296: 1648–1649.

Kimball, John W., "White Blood Cells (leukocytes)," *Kimball's Biology Papers* [online], [retrieved on Dec. 2, 2002]. Retrieved from the internet: <http://users.rcn.com/jkimball.ma.ultranet/BiologyPages/B/Blood.html.; 2 pgs.

Leszek et al., "Colostrinin® proline–rich polypeptide complex from ovine colostrum—a long–term study of its efficacy in Alzheimer's Disease," (2002) *Med Sci Monit;* 8(10):PI93–96.

Rao, "Multipotent and Restricted Precursors in the Central Nervous System," (1999) *The Anatomical Record (New Anat.)*;257:137–148.

Schwab, "Repairing the Injured Spinal Cord," (2002) *Science;* 295:1029–1031.

Boldogh et al., "Modulation of 4HNE–Mediated Signaling by proline–rich peptides form Ovine Colostrum," *J Mol Neuroscience,* May 2003;20(2): 125–134.

Brown et al., "7–Hydroperoxycholesterol and its products in oxidized low density lipoprotein and human atherosclerotic plaque," *J. Lipid Res,* 1997; 38: 1730–1745.

Bruce–Keller et al., "4–Hydroxynonenal, a product of lipid peroxidation, damages cholinergic neurons and impairs visuospatial memory in rats," *J Neuropathol Exp Neurol,* 1998;57: 257–267.

Buettner, G.R., "The pecking order of free radicals and antioxidants: lipid peroxidation, alpha–tocopherol, and ascorbate," *Arch Biochem Biophys,* 1993;300: 535–543.

Cadenas et al., "Mitochondrial free radical generation, oxidative stress, and aging," *Free Radic Biol Med,* 2000;29:222–230.

Camandola et al., "The lipid peroxidation product 4–hydroxy–2,3–nonenal inhibits constitutive and inducible activity of nuclear factor kappa B in neurons," *Brain Res Mol Brain Res,* 2000;85:53–60.

Cheng et al., "Effects on mGST A4 transfection on 4–hydroxynonenal–mediated apoptosis and differentiation of K562 human erythroleukemia cells," *Arch Biochem Biophys,* 1999;372: 29–36.

Davies et al., "Photo–oxidation of proteins and its role in cataractogenesis," *J. Photochem. Photobiol B,* 2001;63: 114–125.

Davis et al., "Cellular thiols and rective oxygen species in drug–induced apoptosis," *J. Pharmacol Exp. Ther,* 2001;296: 1–6.

DeZwart et al., "Biomarkers of free radical damage applications in experimental animals and in humans," *Free Radic Biol Med,* 1999; 26:202–226.

Evan et al., "A matter of life and cell death," *Science,* 1998;281: 1317–1322.

Finkel et al., "Oxidants, oxidative stress and the biology of ageing," *Science,* 1998;281: 1317–1322.

Friguet et al., "Protein degradation by the proteasome and its implications in aging," *Ann N Y Acad Sci,* 2000;908: 143–154.

Gage et al., "Isolation, Characterization, and use of Stem Cells from the CNS," *Annu. Rev. Neurosci,* 1995; 18: 159–92.

Gardner et al., "Development of a peptide antibody specific to human glutathione S–transferase alpha 4–4 (hGSTA4–4) reveals preferential localization in human liver mitochondria," *Arch Biochem Biophys,* 2001;390: 19–27.

Hainut et al., "Redox modulation of p53 conformation and sequence–specific DNA binding in vitro," *Cancer Res,* 1993;53: 4469–4473.

Han et al., "Implication of a small GTPase Rac1 in the activation of c–Jun–N–terminal kinase and heat shock factor in response to heat shock," *J Biol Chem,* 2001; 276:1889–1895.

Hughes et al., "Mediation of nerve growth factor–driven cell cycle arrest in PC12 cells by p53. Simultaneous differentiation and proliferation subsequent to p53 functional inactivation," *J Biol Chem,* 2000;275: 37829–37837.

Janusz et al., "Immunoregulatory properties of synthetic peptides, fragments of a proline–rich polypeptide (PRP) from ovine colostrum," *Molecular Immunology,* Oct. 1987;24(10): 1029–1031.

Keller et al., "Mitochondrial manganese superoxide dismutase prevents neural apoptosis and reduces ischemic brain injury: suppression of peroxynitrite production, lipid peroxidation, and mitochondrial dysfucntion," *J Neurosci,* 1998; 18: 687–697.

Kong et al., "Signal transduction events elicited by natural products: a role of MAPK and caspase pathways in homeostatic response and induction of apoptosis," *Arch Pharm Res,* 2000;23: 1–16.

Kruman et al., "Evidence that 4–hydroxynonenal mediates oxidative stress–induced neuronal apoptosis," *J Neurosci,* 1997;17:5089–5100.

Lafon–Cazal et al., "Nitric oxide, superoxide and peroxynitrite: putative mediators of NMDA–induced cell death in cerebellar granule cells," *Neuropharmacology,* 1993;32: 1259–1266.

Leonarduzzi et al., "Lipid oxidation products in cell signaling," *Free Radic Biol Med,* 2000;28: 1370–1378.

Mattson et al., "Alzheimer's disease. Short Precursor shortens memory," *Nature,* 1997;387: 457–458.

Nakamura et al., "Redox regulation of cellular activation," *Annu Rev Immunol,* 1997;15: 351–369.

Page et al., "4–Hydroxynonenal prevents NF–kappaB activation and tumor necrosis factor expression by inhibiting IkappaB phosphorylation and subsequent proteolysis," *J Biol Chem,* 1999;274:11611–11618.

Parola et al., "HNE interacts directly with JNK isoforms in human hepatic stellate cells," *J Clin Invest,* 1998;102:1942–1950.

Perkins et al., "Association of antioxidants with memory in a multiethnic elderly sample using the Third National Health and Nutrition Examination Survey," *Am J Epidemiol,* 1999;150: 37–44.

Perrig et al., "The relation between antioxidants and memory performance in the old and very old," *J Am Geriatr Soc,* 1997;45: 718–724.

Poli et al., "4–Hydroxynonenal in the pathomechanisms of oxidative stress," *IUBMB Life,* 2000;50: 315–321.

Rivas–Arancibia et al., "Effects of ozone exposure in rats on memory and levels of brain and pulmonary superoxide dismutase," *Environ Res,* 1998;76: 33–39.

Ross et al., "Atherosclerosis: a cancer of the blood vessels?," *Am J Clin Pathol 116 Suppl,* 2001:S97–107.

Rusnak et al., "Sensing electrons: protein phosphatase redox regulation," *Trends Biochem Sci,* 2000;25: 527–529.

Sano et al., "A controlled trial of selegiline, alpha–tocopherol, or both as treatment for Alzheimer's disease," *The Alzheimer's Disease Cooperative Study, N Engl J Med,* 1997;336:1216–1222.

Sayre et al., "4–Hydroxynonenal–derived advanced lipid peroxidation end products are increased in Alzheimer's disease," *J Neurochem,* 1997;68: 2092–2097.

Senft et al., "Determining glutathione and glutathione disulfide using the fluorescense probe o–phthaladehyde," *Anal Biochem,* 2000; 280: 80–86.

Sinclair et al., "Altered plasma antioxidant status in subjects with Alzheimer's disease and vascular dementia," *Int J Geriatr Psychiatry,* 1998;13: 840–845.

Uchida et al., "Modification of histidine residures in proteins by reaction with 4–hydroxynonenal," *Proc Natl Acad Sci USA,* 1992;89:4544–4548.

Vaglini et al., "Cytochrome P450 and parkinsonism: protective role of CYP2E1," *Funct Neurol,* 2001;16: 107–112.

Woods et al., "Regulation of p53 function," *Exp Cell Res,* 2001;264: 56–66.

Yoritaka et al., "Immunohistochemical detection of 4–hydroxynonenal protein adducts in Parkinson disease," *Proc Natl Acad Sci USA,* 1996;93: 2696–2701.

Zimecki et al., "Immunotropic properties of fractions isolated from human milk," *Arch Immunol Ther Exp,* 1984;32:203–209.

Zimecki et al., "The effect of a proline–rich polypeptide (PRP) on the humoral immune response. II. PRP induces differentiation of helper cells from glass–nonadherent thymocytes (NAT) and suppressor cells from glass–adherent thymocytes (GAT)," *Arch Immunol Ther Exp,* 1984;32: 197–201.

Zimecki et al., "The effect of a poline–rich polypeptide (PRP) on the humoral immune response. I. Distinct effect of PRP on the T cell properties of mouse glass–nonadherent (NAT) and glass–adherent (GAT) thymocytes in thymectomized mice," *Arch Immunol Ther Exp,* 1984;32: 191–196.

* cited by examiner

USE OF COLOSTRININ, CONSTITUENT PEPTIDES THEREOF, AND ANALOGS THEREOF FOR INDUCING CYTOKINES

This application claims priority to U.S. Provisional Application Ser. No. 60/420,369, filed Oct. 22, 2002, and is a Continuation-In-Part of U.S. patent application Ser. No. 10/281,652, filed on Oct. 28, 2002, which is a Divisional of U.S. patent application Ser. No. 09/641,803, filed Aug. 17, 2000 (issued on Dec. 31, 2002 as U.S. Pat. No. 6,500,798), which claims the benefit of U.S. Provisional Application Ser. No. 60/149,311, filed Aug. 17, 1999, all of which are incorporated herein by reference.

BACKGROUND OF THE INVENTION

Colostrum is a component of the milk of mammals during the first few days after birth. Colostrum is a thick yellowish fluid and is the first lacteal secretion post parturition and contains a high concentration of immunogloblins (IgG, IgM, and IgA) and a variety of non-specific proteins. Colostrum also contains various cells such as granular and stromal cells, neutrophils, monocyte/macrophages, and lymphocytes. Colostrum also includes growth factors, hormones, and cytokines. Unlike mature breast milk, colostrum contains low sugar, low iron, but is rich is lipids, proteins, mineral salts, vitamins, and immunoglobins.

Colostrum also includes or contains a proline-rich polypeptide aggregate or complex, which is referred to as colostrinin (CLN). One peptide fragment of colostrinin is Val-Glu-Ser-Tyr-Val-Pro-Leu-Phe-Pro (SEQ ID NO:31), which is disclosed in International Publication No. WO-A-98/14473. Colostrinin and this fragment have been identified as useful in the treatment of disorders of the central nervous system, neurological disorders, mental disorders, dementia, neurodegenerative diseases, Alzheimer's disease, motor neurone disease, psychosis, neurosis, chronic disorders of the immune system, diseases with a bacterial and viral aetiology, and acquired immunological deficiencies, as set forth in International Publication No. WO-A-98/14473.

Although certain uses for colostrinin have been identified, it would represent an advancement in the art to discover and disclose other uses for colostrinin, or a component thereof, that are not readily ascertainable from the information currently known about colostrinin or its constituents.

SUMMARY OF THE INVENTION

The present invention relates to the use of colostrinin, at least one constituent (i.e., component) peptide thereof, at least one active analog thereof (e.g., peptide having an N-terminal sequence equivalent to an N-terminal sequence of at least one of the colostrinin constituent peptides), and combinations thereof, as modulators of intracellular signaling mechanisms. The signaling molecules discovered to date that are modulated include 4HNE adduct formation, GSH, P53, and JNK.

Furthermore, the present invention relates to the use of colostrinin, at least one constituent (i.e., component) peptide thereof, at least one active analog thereof (e.g., peptide having an N-terminal sequence equivalent to an N-terminal sequence of at least one of the colostrinin constituent peptides), and combinations thereof, in the inhibition of apoptosis. Specifically, the apoptotic (cytotoxic) effect of B amyloid on SH-SY5Y neuronal cells and TNF-alpha.

In one embodiment, the present invention provides a method of modulating an intracellular signaling molecule in a cell. The method includes contacting the cell with a modulator selected from the group of colostrinin, a constituent peptide thereof, an active analog thereof, and combinations thereof, under conditions effective to accomplish at least one of the following: reduce 4HNE-protein adduct formation; inhibit 4HNE-mediated glutathione depletion; inhibit 4HNE-induced activation of p53 protein; or inhibit 4HNE-induced activation of c-Jun NH2-terminal kinases.

In one embodiment, the present invention provides a method of down regulating 4HNE-mediated lipid peroxidation in a cell. The method includes contacting the cell with a modulator selected from the group of colostrinin, a constituent peptide thereof, an active analog thereof, and combinations thereof, wherein: the active analog is an active analog of a constituent peptide of colostrinin selected from the group of SEQ ID NO:1 through SEQ ID NO:34; the active analog comprises a peptide having an amino acid sequence with at least about 15 percent proline and having at least about 70 percent structural similarity to one or more constituent peptides of colostrinin; and the active analog does not interfere with cellular uptake of redox-sensitive 2',7'-dihydro-dichlorofluorescein-diacetate.

In one embodiment, the present invention provides a method for inhibiting apoptosis in a cell (typically, due to DNA damage). The method includes contacting the cell with an effective amount of an apoptosis inhibitor selected from the group of colostrinin, a constituent peptide thereof, an active analog thereof, and combinations thereof.

In another embodiment of inhibiting apoptosis in a cell, a method is provided that includes contacting the cell with an effective amount of an apoptosis inhibitor selected from the group of colostrinin, a constituent peptide thereof, an active analog thereof, and combinations thereof, wherein; the active analog is an active analog of a constituent peptide of colostrinin selected from the group of SEQ ID NO:1 through SEQ ID NO:34; the active analog comprises a peptide having an amino acid sequence with at least about 15 percent proline and having at least about 70 percent structural similarity to one or more constituent peptides of colostrinin; and the active analog does not interfere with cellular uptake of redox-sensitive 2',7'-dihydro-dichlorofluorescein-diacetate.

Other methods of the present invention include protecting against DNA damage in a cell, and reducing the toxic effect of β-amyloid or retinoic acid on a cell. These methods involve contacting the cell with an effective amount of a compound selected from the group of colostrinin, a constituent peptide thereof, an active analog thereof, and combinations thereof.

The cell can be present in a cell culture, a tissue, an organ, or an organism. For certain embodiments, the cell is a mammalian cell. For certain embodiments, the cell is a human cell.

For certain embodiments, the compound (e.g. modulator such as an apoptosis inhibitor) is a constituent peptide of colostrinin. Preferably, the modulator is selected from the group of MQPPPLP (SEQ ID NO:1), LQTPQPLLQVM-MEPQGD (SEQ ID NO:2), DQPPDVEKPDLQPFQVQS (SEQ ID NO:3), LFFFLPVVNVLP (SEQ ID NO:4), DLEMPVLPVEPFPFV (SEQ ID NO:5), MPQN-FYKLPQM (SEQ ID NO:6), VLEMKFPPPPQETVT (SEQ ID NO:7), LKPFPKLKVEVFPFP (SEQ ID NO:8), VVMEV (SEQ ID NO:9), SEQP (SEQ ID NO:10), DKE (SEQ ID NO:11), FPPPK (SEQ ID NO:12), DSQPPV (SEQ ID NO:13), DPPPPQS (SEQ ID NO:14), SEEMP (SEQ ID NO:15), KYKLQPE (SEQ ID NO:16), VLPPNVG (SEQ ID NO:17), VYPFTGPIPN (SEQ ID NO:18), SLPQNILPL (SEQ ID NO:19), TQTPVVVPPF (SEQ ID NO:20), LQPE-IMGVPKVKETMVPK (SEQ ID NO:21), HKEMPFP-KYPVEPFTESQ (SEQ ID NO:22), SLTLTDVEKLHL-PLPLVQ (SEQ ID NO:23), SWMHQPP (SEQ ID NO:24), QPLPPTVMFP (SEQ ID NO:25), PQSVLS (SEQ ID NO:26), LSQPKVLPVPQKAVPQRDMPIQ (SEQ ID NO:27), AFLLYQE (SEQ ID NO:28), RGPFPILV (SEQ ID NO:29), ATFNRYQDDHGEEILKSL (SEQ ID NO:30), VESYVPLFP (SEQ ID NO:31), FLLYQEPVLGPVR (SEQ ID NO:32), LNF (SEQ ID NO:33), and MHQPPQ-PLPPTVMFP (SEQ ID NO:34), and combinations thereof.

As used herein, "a" or "an" means one or more (or at least one), such that combinations of active agents (i.e., active oxidative stress regulators), for example, can be used in the compositions and methods of the invention. Thus, a composition that includes "a" polypeptide refers to a composition that includes one or more polypeptides.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE DRAWINGS

The invention can be better understood with reference to the following detailed description together with the appended illustrative drawings in which like elements are numbered the same.

DETAILED DESCRIPTION OF ILLUSTRATIVE EMBODIMENTS

Figure 1A:
FIG. 1. Colostrinin inhibits formation of protein-HNE (i.e., 4-HNE protein) adducts. (A): 4HNE (25 nM); (B): $H_2O_2$ (100 µM); (C): CLN(10 µg/ml) pre-treatment followed by 4HNE (25 nM) exposure; (D): LAH (10 µg/ml) pre-treatment followed by 4HNE (25 nM) exposure; (E): HNE-protein adducts detected by Western blot analysis. Lane 1, 25 nM; lane 2, 12.5 nM; lane 3, 6.2 nM of 4HNE alone; lanes 4–6, CLN (10 µg/ml) plus 4HNE, 25, 12.5 and 6.2 nM, respectively.

Colostrinin, a complex of proline-rich polypeptides derived from ovine colostrum, induces mitogenic stimulation and a variety of cytokines in human peripheral blood leukocytes. It also possesses anti-oxidant activity in pheochromocyltoma (PC12) cells.

It has been discovered that colostrinin, at least one constituent peptide thereof, and/or at least one active analog thereof (e.g., a peptide having an N-terminal sequence equivalent to an N-terminal sequence of at least one of the colostrinin constituent peptides) can be used as modulators of intracellular signaling mechanisms. The signaling molecules discovered to date that are modulated include 4HNE adduct formation, GSH, P53, and JNK.

More specifically, the present invention provides methods that involve: 1) reduction of the abundance of 4HNE-protein adducts as shown by fluorescent microscopy and Western blot analysis; 2) reduction of intracellular levels of ROS as shown by a decrease in 2',7'dichlorodihydro-fluorescein-mediated fluorescence; 3) inhibition of 4HNE-mediated glutathione depletion as determined fluorimetrically; and 4) inhibition of 4HNE-induced activation of c-Jun NH2-terminal kinases. Furthermore, the present invention provides methods that down regulate the 4HNE-mediated lipid peroxidation and its product-induced signaling that otherwise may lead to pathological changes at the cellular and organ level.

Also, the present invention relates to the use of colostrinin, at least one constituent (i.e., component) peptide thereof, at least one active analog thereof (e.g., peptide having an N-terminal sequence equivalent to an N-terminal sequence of at least one of the colostrinin constituent peptides), and combinations thereof, in the inhibition of apoptosis, specifically, the inhibition is related to the apoptotic (cytotoxic) effect of β-amyloid on SH-SY5Y neuronal cells and TNF-alpha or the apoptotic effect of retinoic acid.

Such compounds (e.g. modulators such as inhibitors) are referred to herein as "active agents." Significantly, such active agents can be administered alone or in various combinations to a patient (e.g., animals including humans) as a medication or dietary (e.g., nutrient) supplement in a dose sufficient to produce the desired effect throughout the patient's body, in a specific tissue site, or in a collection of tissues (organs).

Colostrinin is composed of peptides, the aggregate of which has a molecular weight range between about 5.8 to about 26 kiloDaltons (kDa) determined by polyacrylamide gel electrophoresis. It has a greater concentration of proline than any other amino acid. Ovine colostrinin has been found to have a molecular weight of about 18 kDa and includes three non-covalently linked subunits having a molecular weight of about 6 kDa and has about 22 wt-% proline.

Colostrinin has been found to include a number of peptides ranging from 3 amino acids to 22 amino acids or more. These can be obtained by various known techniques, including isolation and purification involving eletrophoresis and synthetic techniques. The specific method of obtaining colostrinin and SEQ ID NO:31 is described in International Publication No. WO 98/14473. Using HPLC and Edelman Degradation, over 30 constituent peptides of colostrinin have been identified, which can be classified into several groups: (A) those of unknown precursor; (B) those having a β-casein homologue precursor; (C) those having a β-casein precursor; and (D) those having an annexin precursor. These peptides are described in International Patent Publication No. WO 00/75173, published Dec. 14, 2000, and can be synthesized according to well-known synthetic methods. These peptides (i.e., constituent peptides of colostrinin), which can be derived from colostrinin or chemically synthesized, include: MQPPPLP (SEQ ID NO:1); LQTPQ-PLLQVMMEPQGD (SEQ ID NO:2); DQPPPDVEKP-DLQPFQVQS (SEQ ID NO:3); LFFFLPVVNVLP (SEQ ID NO:4); DLEMPVLPVEPFPFV (SEQ ID NO:5); MPQN-FYKLPQM (SEQ ID NO:6); VLEMKFPPPPQETVT (SEQ ID NO:7); LKPFPKLKVEVFPFP (SEQ ID NO:8); VVMEV (SEQ ID NO:9); SEQP (SEQ ID NO:10); DKE (SEQ ID NO:11); FPPPK (SEQ ID NO:12); DSQPPV (SEQ ID NO:13); DPPPPQS (SEQ ID NO:14); SEEMP (SEQ ID NO:15); KYKLQPE (SEQ ID NO:16); VLPPNVG (SEQ ID NO:17); VYPFTGPIPN (SEQ ID NO:18); SLPQNILPL (SEQ ID NO:19); TQTPVVVPPF (SEQ ID NO:20); LQPE-IMGVPKVKETMVPK (SEQ ID NO:21); HKEMPFP-KYPVEPFTESQ (SEQ ID NO:22); SLTLTDVEKLHL-PLPLVQ (SEQ ID NO:23); SWMHQPP (SEQ ID NO:24); QPLPPTVMFP (SEQ ID NO:25); PQSVLS (SEQ ID NO:26); LSQPKVLPVPQKAVPQRDMPIQ (SEQ ID NO:27); AFLLYQE (SEQ ID NO:28); RGPFPILV (SEQ ID NO:29); ATFNRYQDDHGEEILKSL (SEQ ID NO:30); VESYVPLFP (SEQ ID NO:31); FLLYQEPVLGPVR (SEQ ID NO:32); LNF (SEQ ID NO:33); and MHQPPQ-PLPPTVMFP (SEQ ID NO:34). These can be classified as follows: (A) those of unknown precursor include SEQ ID NOs:2, 6, 7, 8, 10, 11, 14, and 33; (B) those having a β-casein homologue precursor include SEQ ID NOs:1, 3, 4, 5, 9, 12, 13, 15, 16, 17, and 31; (C) those having a β-casein precursor include SEQ ID NOs:18 (casein amino acids 74–83), 19 (casein amino acids 84–92), 20 (casein amino acids 93–102), 21 (casein amino acids 103–120), 22 (casein amino acids 121–138), 23 (casein amino acids 139–156), 24 (casein amino acids 157–163), 25 (casein amino acids 164–173), 26 (casein amino acids 174–179), 27 (casein amino acids 180–201), 28 (casein amino acids 202–208), 29 (casein amino acids 214–222), 32 (casein amino acids 203–214), and 34 (casein amino acids 159–173); and (D) those having an annexin precursor include SEQ ID NO:30 (annexin amino acids 203–220).

A preferred group of such peptides includes: MQPPPLP (SEQ ID NO:1); LQTPQPLLQVMMEPQGD (SEQ ID NO:2); DQPPDVEKPDLQPFQVQS (SEQ ID NO:3); LFF-FLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPFP-KLKVEVFPFP (SEQ ID NO:8); and combinations thereof.

The polypeptides of SEQ ID NOs:1–34 can be in their free acid form or they can be amidated at the C-terminal carboxylate group. The present invention also includes analogs of the polypeptides of SEQ ID NOs:1–34, which includes polypeptides having structural similarity with SEQ ID NOs:1–34. These peptides can also form a part of a larger peptide. An "analog" of a polypeptide includes at least a portion of the polypeptide, wherein the portion contains deletions or additions of one or more contiguous or non-contiguous amino acids, or containing one or more amino acid substitutions. An "analog" can thus include additional amino acids at one or both of the terminii of the polypeptides listed above. Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, (γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Preferably, the active analogs of colostrinin and its constituent peptides include polypeptides having a relatively large number of proline residues. Because proline is not a common amino acid, a "large number" preferably means that a polypeptide includes at least about 15% proline (by number), and more preferably at least about 20% proline (by number). Most preferably, active analogs include more proline residues than any other amino acid.

As stated above, active analogs of colostrinin and its constituent peptides include polypeptides having structural similarity. Structural similarity is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, available at http://www.ncbi.nlm.nih.gov/gorf/b12.html. Preferably, the default values for all BLAST 2 search parameters are used, including matrix=BLOSUM62; open gap penalty=11, extension gap penalty=1, gapx_dropoff=50, expect=10, wordsize=3, and filter on. In the comparison of two amino acid sequences using the BLAST search algorithm, structural similarity is referred to as "identity." Preferably, an active analog of colostrinin or its constituent peptides has a structural similarity to colostrinin or one or more of its constituent peptides (preferably, one of SEQ ID NOs:1–34) of at least about 70% identity, more preferably, at least about 80% identity, and most preferably, at least about 90% identity.

Colostrinin or any combination of its peptide components or active analogs thereof can be derived (preferably, isolated and purified) naturally such as by extraction from colostrum or can be synthetically constructed using known peptide polymerization techniques. For example, the peptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77–183 (1992). Moreover, gene sequence encoding the colostrinin peptides or analogs thereof can be constructed by known techniques such as expression vectors or plasmids and transfected into suitable microorganisms that will express the DNA sequences thus preparing the peptide for later extraction from the medium in which the microorganism are grown. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The peptides used in the methods of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary, but from about 4 to 8 peptides per carrier molecule are typically obtained under standard coupling conditions.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-carboiimide hydrochloride (EDC; ten times the amount of peptide) is dissolved in a small amount of water. The EDC solution was added to the peptide/ovalbumin mixture and allowed to react for a number of hours. The mixture may then dialyzed (e.g., into phosphate buffered saline) to obtain a purified solution of peptide/ovalbumin conjugate. Peptide/carrier molecule conjugates prepared by this method typically contain about 4 to 5 peptides per ovalbumin molecule.

The present invention also provides a composition that includes one or more active agents (i.e., colostrinin, at least one constituent peptide thereof, or active analog thereof) of the invention and one or more carriers, preferably a pharmaceutically acceptable carrier. The methods of the invention include administering to, or applying to the skin of, a patient, preferably a mammal, and more preferably a human, a composition of the invention in an amount effective to produce the desired effect. The active agents of the present invention are formulated for enteral administration (oral, rectal, etc.) or parenteral administration (injection, internal pump, etc.). The administration can be via direct injection into tissue, interarterial injection, intervenous injection, or other internal administration procedures, such as through the use of an implanted pump, or via contacting the composition with a mucus membrane in a carrier designed to facilitate transmission of the composition across the mucus membrane such as a suppository, eye drops, inhaler, or other similar administration method or via oral administration in the form of a syrup, a liquid, a pill, capsule, gel coated tablet, or other similar oral administration method. The active agents can be incorporated into an adhesive plaster, a patch, a gum, and the like, or it can be encapsulated or incorporated into a bioerodible matrix for controlled release.

The carriers for internal administration can be any carriers commonly used to facilitate the internal administration of compositions such as plasma, sterile saline solution, IV solutions or the like. Carriers for administration through mucus membranes can be any well-known in the art. Carriers for administration oral can be any carrier well-known in the art.

The formulations may be conveniently presented in unit dosage form and may be prepared by any of the methods well known in the art of pharmacy. All methods include the step of bringing the active agent into association with a carrier which constitutes one or more accessory ingredients. In general, the formulations are prepared by uniformly and intimately bringing the active agent into association with a liquid carrier, a finely divided solid carrier, or both, and then, if necessary, shaping the product into the desired formulations.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. The amount of active agent is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, DMSO, polyhydroxy alcohols, or other bases used for topical pharmaceutical formulations.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

EXAMPLES

The invention will be further described by reference to the following detailed examples. The examples are meant to provide illustration and should not be construed as limiting the scope of the present invention.

Examples 1–5

Materials and Methods

Cell cultures: Pheochromocytoma (PC12) cells were provided by Dr. Regino Perez-Polo (University of Texas Medical Branch, Department of Human Biological Chemistry and Genetics) and maintained in EMEM supplemented with 10% fetal bovine serum, penicillin (100 IU/ml) and streptomycin (100 micrograms per milliliter ($\mu$g/ml)). Exponentially growing populations of PC12 cells were sub-cultured and used for all experiments.

Western blot analysis: PC12 cells were plated at $7\times10^6$ cells/T75 flask. After exposure to 4HNE, colostrinin or their combination, cells were collected and lysed in 50 millimolar (mM) Tris, 5 mM EDTA, 150 mM NaCl, 0.5% NP-40, 10% glycerol and protease inhibitor cocktail (supplemented with 1 mM $Na_3VO_4$, 2 mM EDTA, 1 mM phenylmethylsulfonyl fluoride). Lysates were centrifuged at 14,000 g for 10 minutes (min) (4° C.) and 40 $\mu$g of protein was fractionated on a 10% SDS-polyacrylamide gel and transferred to protein-optimized membranes (Amersham, Inc.). p53 was detected using specific antibody (DO1; Santa Cruz Biotechnology, Inc.) at a dilution of 1:300. Adducts were detected using an antibody to HNE-protein adducts (Pharmingen, Inc.) at a dilution of 1:500. The anti-phospho-JNK antibody (New England Biolabs, Inc., Beverly, Mass.) was raised against a synthetic phosphopeptide (SFMMT*PY*VVRYYR) corresponding to residues 179–193 of INK. For visualization of primary antibody binding, all blots were incubated with horseradish peroxidase conjugated secondary antibody (Amersham, Inc.) at a dilution of 1:2000, followed by chemiluminescence detection (Amersham, Inc.) and autoradiography.

Immunocytochemistry: PC12 cells grown on cover-slips were fixed overnight in PBS containing 2% paraformaldehyde at 4° C. Cells were permeabilized by 0.3% Triton X-100, washed in PBS then incubated with primary antibody in PBS containing 0.05% Tween 20 (PBS-T). After washing 3 times in PBS-T, FITC-labeled anti-rabbit IgG (Santa Cruz Biotechnology Inc.) was added. Cells were washed (5 times, for 10 min) with PBS-T and mounted on microscope slides in anti-fade solution (Dako, Inc.). Images of cellular immunofluorescence were acquired using a NIKON Eclipse TE300 scanning microscope.

Measurement of glutathione (GSH): In brief, PC12 cells were mock- or pre-treated with CLN or lactalbumin hydrolysate (LAH), both in 10 $\mu$g/ml concentration and then exposed to 4HNE (25 nM). PBS-washed (twice) cells were then extracted with 25% (w/v) metaphosphoric acid solution containing 5 mM EDTA. After ultracentrifugation (105,000 g for 30 min), 100 $\mu$l of 100 mM phosphate solution (pH 8.0) containing 5 mM EDTA and 10 $\mu$l of o-phthalaldehyde OPA(OPD; Molecular Probes, Inc.) was added to the supernatant, and the fluorescence intensity at 420 nm determined with excitation set at 350 nm (A. P. Senft et al., *Anal Biochem.*, 280:80–86 (2000)).

Flow cytometry: Relative changes in ROS levels were determined as described previously (I. Boldogh et al., *Psychogeriatr Ann*, 4:57–65 (2001)). Briefly, PC12 cells at 70% confluence were trypsinized and washed with EMEM containing 10% FBS. Cells were re-suspended in EMEM (plus 5% FBS) and loaded with 2',7'dichlorodihydro-fluorescein diacetate ($H_2$DCF-DA; Molecular Probes Inc.) (5 mM final concentration) for 15 min, at 37° C. then washed in growth medium. Following centrifugation, the cell pellets were re-suspended in EMEM containing 10 mM HEPES (pH: 7.4). DCF-mediated fluorescence of treated and mock-treated cells was determined by flow cytometry (Becton Dickinson FACS Scan) using 488 nm and 525 nm excitation and emission settings, respectively. Each data point represents the mean fluorescence for 12,000 cells.

Reagents: Colostrinin (CLN) was purified from ovine colostrum, collected during the first milking (6–12 hours (hr) after lambing), according to the method developed by Janusz et al. (M. Janusz et al., *FEBS Lett.*, 49:276–279 (1974)). A high content of proline (>23%) and lack of detectable alanine, arginine, histidine, tryptophan, methionine, and cysteine were confirmed by amino acid analysis of CLN. A peptide control was prepared by trypsin (Sigma-Aldrich) digestion of purified lactalbumin from bovine milk (Sigma). The trypsin was then inhibited by treatment with inhibitor (Invitrogen). SDS-PAGE conformed digestion of lactalbumin into peptides, and the hydrolysate was referred to as LAH.

Statistical analysis: The experiments were repeated at least three times and statistically analyzed for significant differences using ANOVA procedures and Student's t-tests. Data are expressed as means±S.E.

Examples 1–5

Results

Example 1

Colostrinin Reduces 4HNE-Protein Adduct Formation in PC 12 Cells

Figure 1B:
Figure 1C:
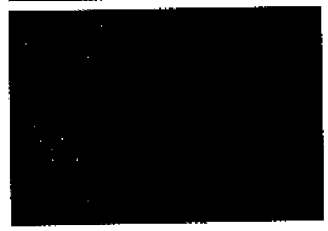

Fluorescent microscopy and Western blot analysis was undertaken to investigate the extent of 4HNE protein-adduct formation in cultures of PC12 cells in the presence of CLN. Cells were pretreated with CLN or LAH in the presence or absence of 4HNE and then analyzed for the formation of 4HNE-protein adducts. The results in FIGS. 1A and 1B show that addition of 4HNE (25 nanomolar (nM)) or $H_2O_2$ (100 micromolar ($\mu$M) resulted in a bright fluorescence, localized to the cytoplasmic region of PC12 cells due to binding of antibody to 4HNE-protein adducts. When cells were pre-treated with CLN (10 microgram per milliliter ($\mu$g/ml)) for 15 minutes (min) and exposed to 4HNE (25 nM) for 15 min (concentrations of CLN and time required for effect were determined in preliminary studies), the results indicated that CLN reduced fluorescence intensity (FIG. 1C) to background level (data not shown). In the controls, pre-treatment of cells with an N-acetyl-L-cysteine (10 mM) and trolox (1 mM; a water-soluble-tocopherol) combination significantly reduced 4HNE-mediated intracellular fluorescence.

Figure 1D:

To determine whether the inhibitory effect of CLN was specific, CLN was substituted with digested lactalbumin hydrolysate (LAH, Materials and Methods), which contains a variety of peptides as does CLN. Results in FIG. 1D show bright fluorescence in cells treated with LAH (10 $\mu$g/ml) plus 4HNE (25 nM), which is similar to that seen with 4HNE alone (FIG. 1A). These data indicate that CLN inhibits adduct formation, and the effect is specific and could be the result of a not yet-determined interaction between its constituent peptides and cellular component(s).

Figure 1E:
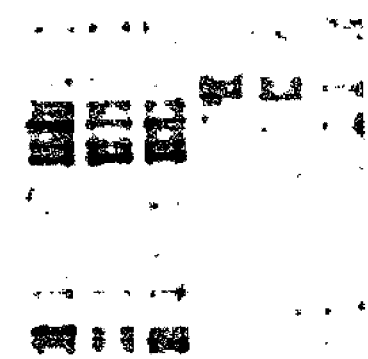

To confirm the results generated by immunochemistry, Western blot analysis was used to investigate changes in 4HNE-protein adduct levels in cells treated with 4HNE alone or CLN plus 4HNE. FIG. 1E (lanes 1, 2, and 3) shows that 4HNE alone induced a significant increase in levels of 4HNE-protein adducts, with molecular weights ranging from 200 kD to 15 kD. CLN (10 µg/ml) abolished adduct formation, as shown in FIG. 1E lanes 4 to 6. Overall these data indicate that CLN can block the formation of 4HNE-adducts. From these results, it is believed that the inhibition of 4HNE-protein adduct formation by CLN is multi-factorial and may involve mechanisms such as direct scavenging (binding) of 4HNE via cysteine, lysine, or histidine residues in CLN, or by inhibition of 4HNE's entry onto cells.

To determine whether CLN can protect mitochondria and abolish the oxidative stress induced by 4HNE, PC12 cells were treated with CLN (with LAH as control) and/or 4HNE and the changes in ROS levels were monitored by the redox-sensitive 2',7'-dichlorofluorescein diacetate ($H_2$DCF-DA) probe (1. Boldogh et al., *Psychogeriatr Ann*, 4:57–65 (2001); LeBel, *Chem. Res. Toxicol.*, 5:227–231 (1992)). Mock-as well as CLN (or LAH) pre-treated cells were loaded with $H_2$DCF-DA then exposed to 4HNE for 15 min. Changes in fluorescence intensities mediated by the oxidized probe, DCF, were determined by flow cytometry. Prior to data collection, propidium iodide was added to the samples for sorting out nonviable cells.

Example 2

Colostrinin Affects the Oxidative Metabolism in PC12 Cells

Figure 2A:
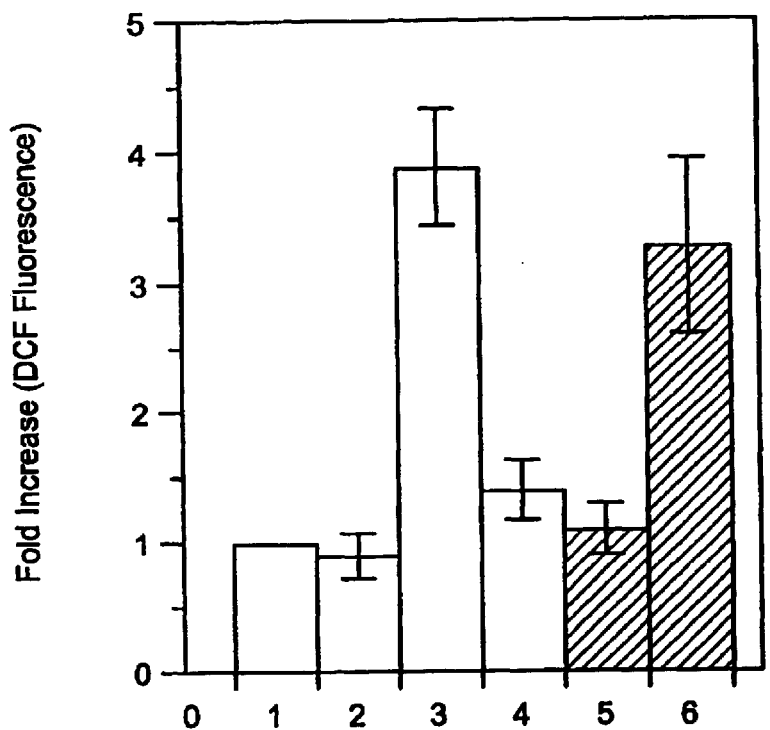
FIG. 2. Colostrinin inhibits 4HNE-induced oxidative stress. (A): 1, control; 2, colostrinin (10 µg/ml); 3, 4HNE (25 µM); 4, 4HNE (25 nM) plus colostrinin (10 µg/ml); 5, lactalbumin hydrolysate (10 µg/ml); 6, lactalbumin hydrolysate (10 µg/ml) plus 4HNE (25 nM). (B): A representative FACS histogram of fluorescence of cells treated with 4HNE (25 nM) and CLN (10 µg/ml) plus 4HNE.
Figure 2B:
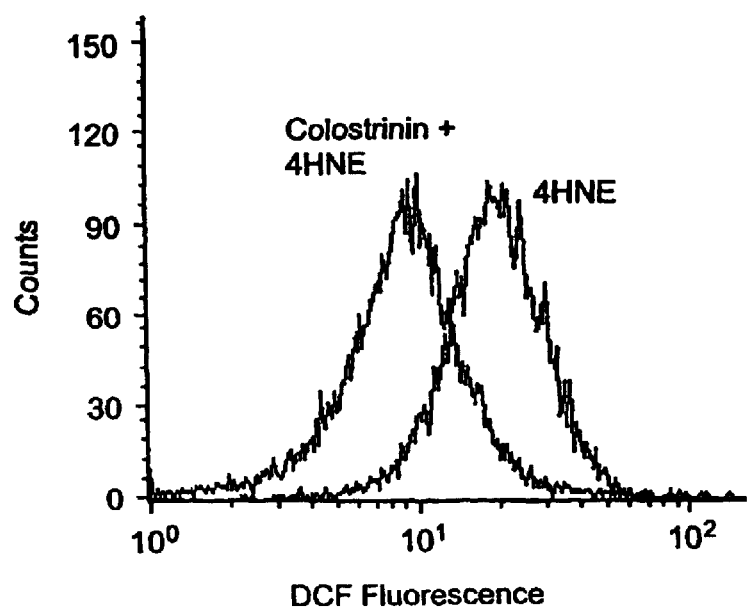

A representative histogram showing the effects of the treatments on ROS levels is shown in FIG. 2B. As summarized in FIG. 2A, 4HNE (25 nM) induced a 4- to 5-fold increase in DCF-mediated fluorescence, while CLN alone or LAH showed no significant effect. Remarkably, CLN abolished (while LAH had no significant effect on) $H_2$DCF oxidation in 4HNE-treated PC 12 cells. Because constituent peptides in LAH did not alter 4HNE-induced $H_2$DCF oxidation, it can be concluded that the effect of CLN is specific, and may protect cells from ROS damage via its quantitatively unique and specific peptide composition.

Example 3

Effect of CLN on 4HNE-Induced Loss of Intracellular GSH Levels

Figure 3:
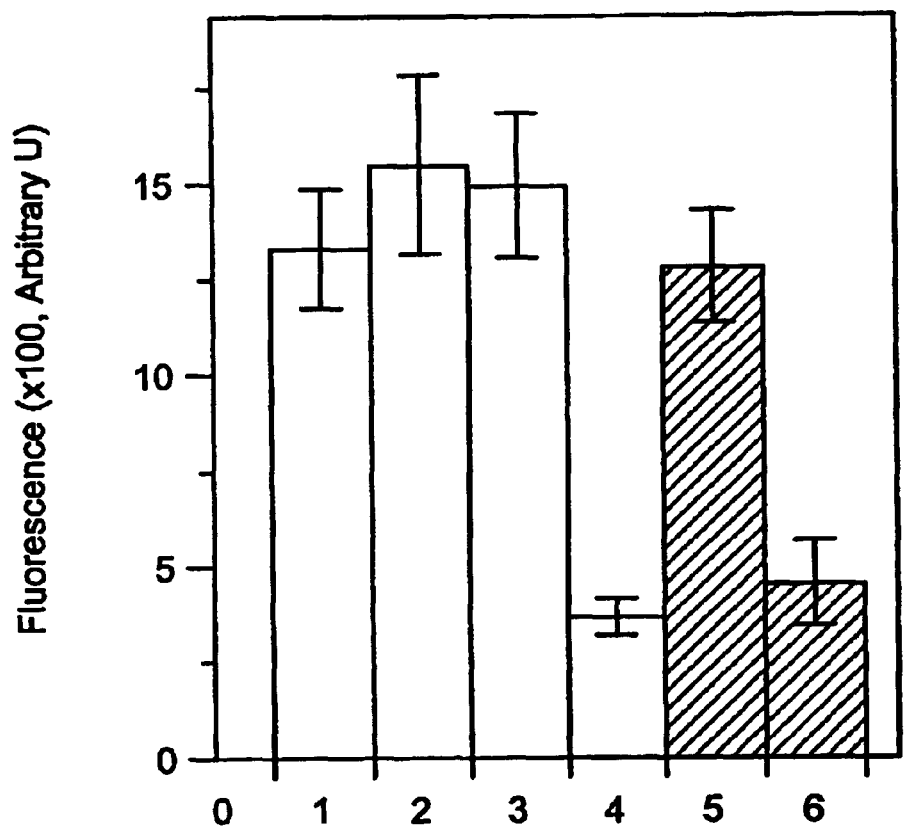
FIG. 3. Effect of CLN on 4HNE-induced loss of intracellular GSH levels. Cells were mock-treated or treated with CLN (or LAH) and/or 4HNE for 30 min, and o-phthalaldehyde-mediated fluorescence was determined as described in Materials and Methods. Open columns: 1, mock-treated; 2, CLN (10 µg/ml)-; 3, LAH (10 µg/ml)-; 4, 4HNE (25 nM)-treated. Filled solid columns: 5, CLN (10 µg/ml) pre- and 4HNE (25 nM)-treated for 30 min; 6, LAH (10 µg/ml) pre- and 4HNE (25 nM)-treated for 30 min.

To investigate whether the anti-oxidant effect of CLN was due to protection of intracellular GSH levels, PC12 cells were per-treated (with CIN or LAH) and exposed to 4HNE, as described above, and changes in GSH levels were determined fluorimetrically. The results summarized in FIG. 3 show that treatment with 4HNE alone for 30 min (time determined in preliminary studies) resulted in a significant reduction of intracellular GSH levels as shown by a change in OPA-GSH's fluorescence. OPA (o-phthalaldehyde or phthalic dicarboxaldehyde) is highly fluorescent when it is conjugated to GSH (A. P. Senft et al., *Anal Biochem.*, 280:80–86 (2000)). Pre-treatment of cells with CLN (10 µg/ml), however, significantly inhibited this change in OPA fluorescence (loss of GSH) while LAH had an insignificant effect.

To determine whether the loss of intracellular GSH was due to it's extrusion from the cells or oxidation, the level of reduced GSH in the extra-cellular fluid was evaluated. Relative to CLN- or mock-treated cells, 4HNE caused a significant increase in OPA-GSH-mediated fluorescence when it was added to extracellular fluid (data not shown). LAH alone or LAH in 4HNE-exposed cells did not affect GSH extrusion (OPA-GSH fluorescence). OPA did not show fluorescence when it was mixed with CLN, LAH or 4HNE alone. These results indicate that CLN mediates its effect on GSH metabolism at the cell membrane level.

Example 4

4HNE-Induced Activation of JNK is Suppressed by CLN

The effect of CLN on 4HNE-induced activation of JNK in PC12 cells was investigated. The activation of JNK was monitored by Western blot analysis using a highly specific anti-phospho-(Tbr-183/Tyr-185) JNK antibody (Materials and Methods).

Figure 4:
FIG. 4. Inhibition of JNK induction by colostrinin. A change in JNK's phosphotyrosine levels was monitored by SDS-PAGE analysis. Equal amounts of protein (50 µg) were fractionated, blotted, and probed with anti-phospho-(Thr-183/Tyr-185)-JNK antibody. Lanes 1 and 2, mock-treated cells; lane 3, 8-(4-chlorophenylthio)-cAMP, an inhibitor of JNK activation; lanes 4 and 5, 25 nM 4HNE; lane 6, CLN (10 µg/ml) alone; lane 7, 25 nM 4HNE plus 10 µg/ml CLN; lane 8, 25 nM 4HNE plus 1 µg/ml CLN; lane 9, 25 nM 4HNE plus 0.1 µg/ml CLN.

The data summarized in FIG. 4 show that 4HNE alone is a potent inducer of JNK phosphorylation (FIG. 4, lanes 4 and 5). Pretreatment of PC12 cells with CLN (1 and 10 µg/nM) or with an inhibitor of JNK activation [8-(4-chlorophenylthio)-cAMP] prevented 4HNE-induced JNK phosphorylation; 4HNE-mediated phosphorylation was reduced by 10 and 1.0 µg/ml CLN (FIG. 4, lanes 7 and 8) to control levels (FIG. 4 lanes 1 and 2). CLN at 0.1 µg/ml concentration did not significantly effect 4HNE-mediated JNK phosphorylation (lane 9). The maximum level of phosphorylation of JNK in 4HNE-treated cells occurred between 15 and 30 min post-treatment as determined in preliminary studies (data not shown). These data indicate that CLN may modulate oxidative metabolism (GSH levels, 4HNE-protein adduct formation) of cells potentially through JNK, a kinase that is central to the cellular stress responses.

Example 5

Colostrinin Inhibits 4HNE-Induced Activation of p53

Figure 5:
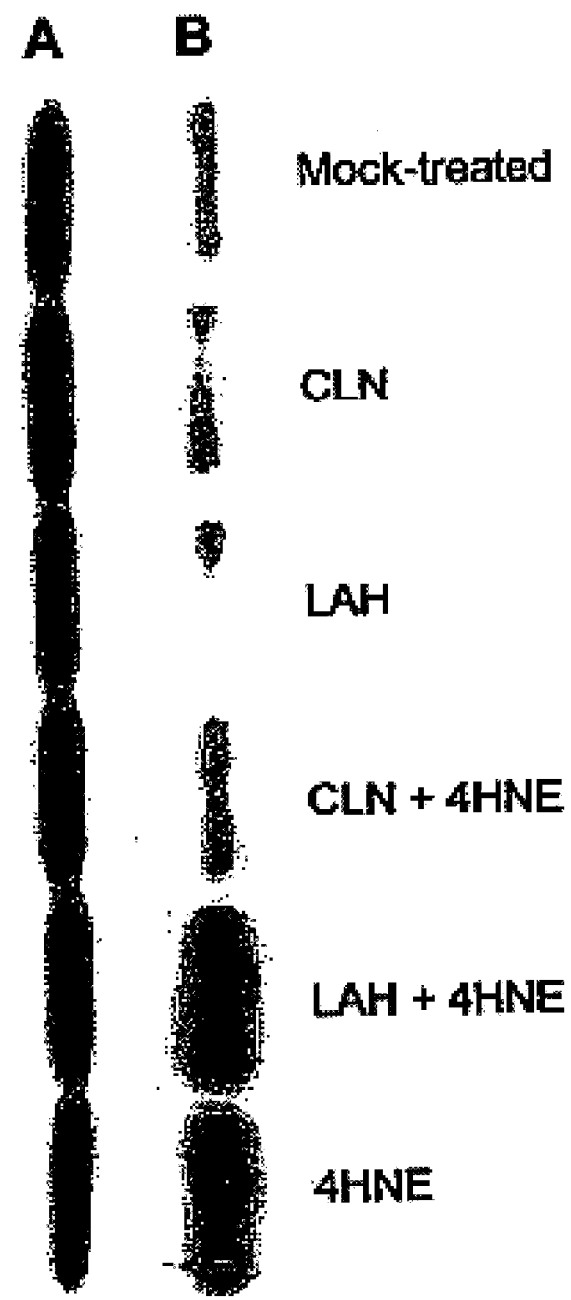
FIG. 5. CLN reduces 4HNE-mediated activation of p53. PC12 cells were pre-treated with CLN or LAH and exposed to 4HNE. Three hours after treatment, cell lysates were analyzed by Western blot analysis. (B) p53; (A) corresponding α-tubulin. 4HNE (25 nM), CLN (10 µg/ml), LAH (10 µg/ml).

Whether CLN could modulate p53 levels after 4HNE exposure was also investigated. In FIG. 5, Western blot analysis shows that CLN reduces activation of p53 induced by 4HNE when compared to cells treated with 4HNE alone. On the other hand, pre-treatment with the same concentration (10 µg/ml) of LAH had no affect on 4HNE-mediated p53 induction. These data suggest that CLN, via its antioxidant activity, can effect activation of p53, a key regulator of cell proliferation, differentiation and apoptosis (G. Evan et al., *Science*, 281:1317–1322 (1998)) and may explain multiple biological effects (antioxidant, differentiation) of CLN.

Examples 1–5

Discussion

It has been shown that CLN, a milk-derived peptide complex can modulate both cytokine production and cellular redox status. To study CLN's antioxidant effects, 4HNE was used for treatment of PC12 cells. 4HNE is a 3-unsaturated aldehyde generated endogenously during lipid peroxidation, specifically from the oxidative degradation of arachidonic and linoleic acids (H. Esterbauer et al., *Free Raids. Biol. Med.*, 11:81–128 (1991)). Further, 4HNE is involved in both normal and pathophysiological events in cells and tissues that result in various chronic diseases. While micromolar concentrations of 4HNE is cytotoxic, at the nanomolar level it can be involved in activation of the signal transduction pathways. For example, it has been shown that depending on concentration, 4HNE can affect proliferation and induce differentiation or apoptosis in cells.

In the current studies, a concentration of 25 nM 4HNE was used. This did not show toxic effects or induce apoptosis but considerably increased the levels of 4HNE-protein adducts (FIG. 1A) in PC12 cells. Remarkably, it was found that CLN abolished 4HNE-protein adduct formation, while LAH (as control) at the same concentration had no effect indicating CLN's specificity. Due to the presence of a highly electrophilic carbon, 4HNE is a potent alkylating agent able to react with histidine, lysine, serine, cystein, and tyrosine side chains in proteins, and thus modify their functions. Although it was hypothesized that peptides of CLN, via its component amino acid residues, were reacting with 4HNE and chemically reducing its concentration, no direct interaction between CLN's peptide(s) and 4HNE were observed.

4HNE is known to modulate the activities of ATPases, phospholipase C, adenylate cyclase, GTP-binding proteins, and protein kinase C. Furthermore, 4HNE can react with the nucleophilic sites in DNA, mitochondrial proteins and a variety of other nucleophiles, including GSH, resulting in cellular stress responses and oxidative stress. In the present studies, it was demonstrated that that CLN was able to prevent a decrease in 4HNE-induced GSH levels. It is proposed that 4HNE-induced reduction in GSH levels may be due to glutathione-S-transferase (GST)-mediated conjugation of 4-HNE to GSH, or that GSH may be utilized in detoxification reactions of ROS.

Taking into consideration that only 25 nM of 4HNE was used, while intracellular concentrations of GSH are in the 0.5 to 10 mM range, reduction of GSH levels by GST or utilization by glutathione peroxidases may not explain the more than 50% loss of GSH. Therefore, the GSH levels in the extracellular fluid was evaluated. The large reduction in GSH levels (FIG. 3) may be due to extrusion of GSH from cells after 4HNE exposure. Indeed, it has been discovered that an increase in GSH in the extracellular milieu is in response to 4HNE treatment. Most remarkably, CLN was able to prevent this effect of 4HNE.

Although some ROS production in 4HNE-treated cells has been shown to be due to mitochondrial damage, it is believed that the 3- to 4-fold increase in ROS levels were due to GSH extrusion, which resulted in a perturbance of cellular anti-oxidant defenses. Most importantly, CLN, but not LAH, inhibited oxidation of $H_2DCF$ strongly suggesting that CLN is involved in the activation of cellular antioxidant defenses or possesses effective anti-oxidant activity via regulating cellular GSH levels.

4HNE exposures have been reported to be linked with c-Jun NH2-terminal kinases activation and c-Jun phosphorylation. Three groups of mitogen-activated protein (MAP) kinases have been identified in mammals: the extracellular signal-regulated kinase, the p38 MAP kinase, and JNKs (also referred to SAPKs). JNKs are activated by a wide variety of stimuli, including ROS, DNA-damaging agents and inhibitors of protein synthesis, and heat or osmotic shock. These stimuli appear to operate through small G proteins of the Ras and epidermal growth factor (EGF) family receptors and sequential activation of various protein kinases. Targets of the JNK signal transduction pathway include the transcription factors ATF2 and c-Jun. c-Jun binds to the N-terminal region of ATF2 and c-Jun and phosphorylates two sites within the activation domain. These factors are members of the basic leucine zipper group that binds as homo- and heterodimeric complexes to AP-1 and AP-1-like sites in the promoters of many genes and result in increased transcriptional activity.

The present studies show that treatment of PC12 cells with 4HNE causes JNK activation within 15 to 30 min. However, in CLN pretreated cells JNK activation was not only delayed or reduced, it was abolished. CLN was also as potent as 8-(4-chlorophenylthio)-cAMP a specific inhibitor of JNK activation. AP-1 phosphorylation, which is a later event in the JNK signaling pathway is presently under investigation. These findings are consistent with the idea that CLN has the ability to protect cells from oxidative stress and other consequences of 4HNE exposure, including JNK activation, and its down-stream consequences.

The Western blot analysis shown in FIG. 5, clearly demonstrated that p53 is normally present in a latent form and that 4HNE induced its activation. It has been shown that p53 lies at the center of a network of complex redox interactions. In this network, p53 can control the timely production of ROS, but this activity is itself under the control of changes in cellular redox status. Thus, p53 activation in 4HNE-treated PC12 cells can occur in multiple ways: it may be due to 4HNE-induced DNA damage, ROS, and/or activation of cell cycle regulatory kinases. Regardless of the mechanism of p53 activation, CLN showed a potent inhibitory effect.

Figure 6A:
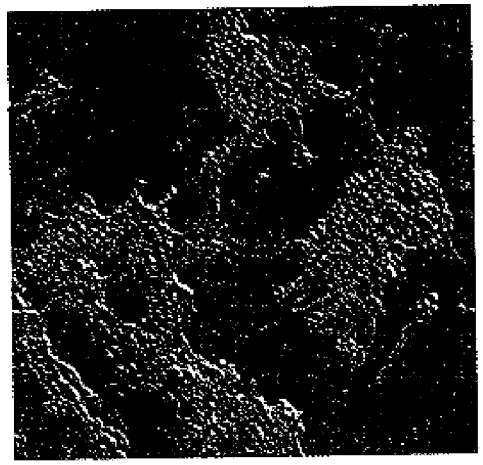
FIGS. 6A–6D. (A) Normal morphology of SH-SY5Y control cells. Cells are mostly clumped, non-contact inhibited (right arrow) with a few elongated cells present. Their refractability indicates they are healthy and growing normally. (B) Cells treated with Beta-amyloid (10 µg/ml added on day 5) that show its toxicity. Note small round granulated cells with little refractability. (C) Differentiated SH-SY5Y cells following treatment with CLN (0.1 µg/ml added on day 5 for 30 minutes). Touching cells are flat, contact inhibited (not clumped), left arrow, and more isolated cells are elongated and neuronal in appearance, right arrow. (D) Cells protected from toxic (apoptotic effect) of Beta-amyloid by treating with CLN (Colostrinin 0.1 µg/ml added on day 5 for 30 minutes+Beta-amyloid 10 µg/ml added on day 5). Cells are flat (upper arrow) or elongated (lower arrow) showing typical morphology of differentiated cells (see FIG. 6C). (E) Inhibition of toxicity (apotetic activity) of Beta-amyloid by CLN treatment (Colostrinin 3 µg/ml added on day 5 for 30 minutes+Beta-amyloid 10 µg/ml added on day 5). Note flattened (bottom arrow) and elongated (upper arrow) cells typical of SH-SY5Y differentiated cells. (F) Toxic (apoptotic) effect of retinoic acid (20 µM added on day 1) on SH-SY5Y cells. The observed toxicity resembles cytopathology induced by viruses. Cytoplasmic bridging caused by shrinking of cells once in contact with each other (upper right arrows), shrunken granular cells (lower right arrow) and small round cells (lower left arrows). (G) Inhibition of toxic effect of retinoic acid by treatment of SH-SY5Y with CLN (20 μM retinoic acid added on day 1+1 μg/ml Colostrinin added on day 5 for 30 minutes). Cells are well organized showing typical morphology of differentiated SH-SY5Y cells, elongation (lower arrow) and flattening (upper arrow).

CLN induced differentiation in SH-SY5Y cells in a dose dependant manner (Table 1A). The ability of CLN to induce differentiation in these cells is shown in FIG. 6A, the control compared to FIG. 6C, a culture treated with 0.1 µg/ml CLN (see figure legends).

Figure 6B:
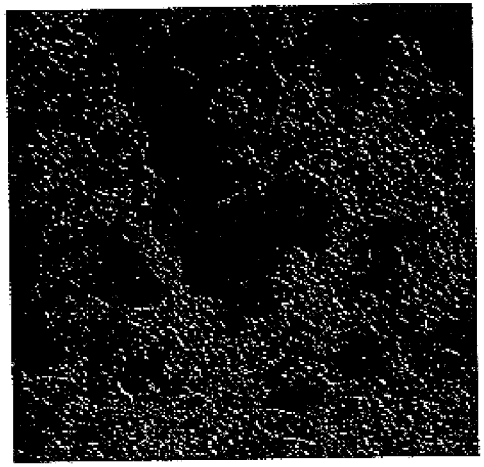
Figure 6C:
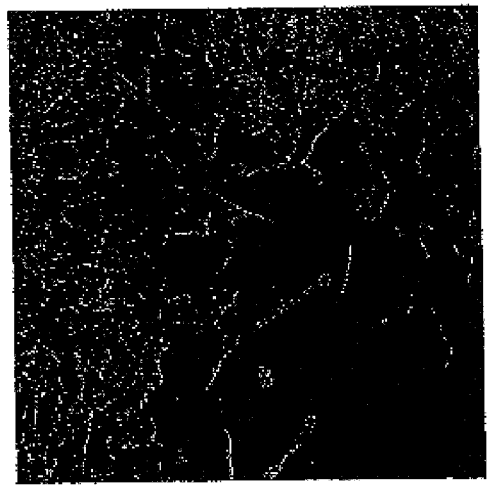
Figure 6D:
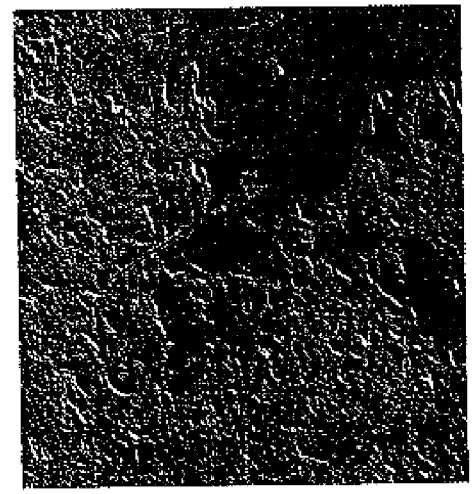
Figure 6E:
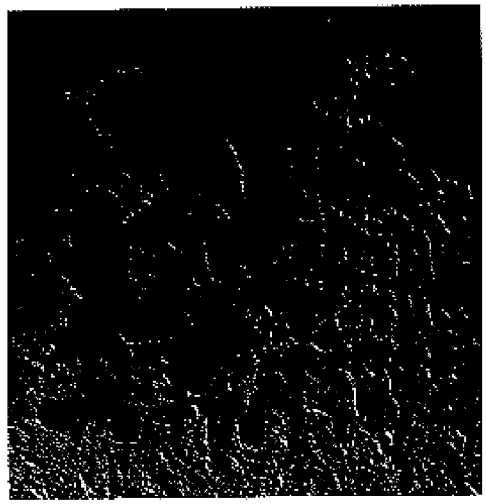

It has been shown that colostrinin can inhibit the toxicity of Beta-amyloid in neural derived SH-SY5Y cells. Essentially complete inhibition of the toxicity occurred at the 0.01 µg/ml level (Table 1B). FIGS. 6D and 6E shows the protective effect of 3.0 and 0.1 µg/ml of CLN on B-amyloid induced toxicity as shown in FIG. 6B. Since this toxicity is the result of the apoptotic activity of Beta-amyloid (β-amyloid), the data indicate that colostrinin is a potent inhibitor of apoptosis in neural-derived cells. This potent activity indicated that even lower concentrations of colostrinin would have to be tested to determine the potency and anti-apoptotic dose response effect of colostrinin in this system. However, a dose dependant development of differentiation did occur in the presence of Beta-amyloid in the colostrinin treated cells (FIGS. 6D and 6E).

The results indicate that not only did colostrinin inhibit the toxicity of Beta-amyloid, but it also was able to induce differentiation of the SH-SY5Y in a dose dependant manner in Beta-amyloid treated cells. This finding indicates that the development of differentiation in Beta-amyloid treated cells could be used as a biological assay for colostrinin and one of its important functions.

To determine whether this was reproducible and to determine the potency of CLN to inhibit retinoic acid toxicity, two concentration of retinoic acid were used to treat cells on day one of the experiment, 20 µM and 40 µM. *Control wells were mock-treated for the duration of the experiment. Retinoic Acid was left on the plate for the duration of the experiment or until washed off. Colostrinin was added to the plate at the indicated doses. When added on Day 1, it was present during the entire experiment. When added on Day 5, it was incubated on the plate for 30 minutes at 37° C. and then removed. The wells were washed twice with PBS before adding β-Amyloid. Cultures were then observed under the microscope and graded.

Figure 6F:
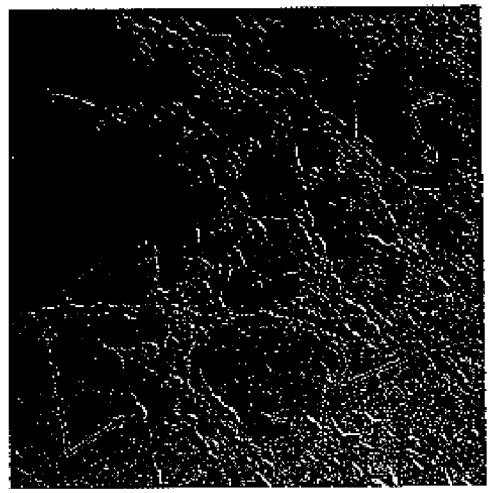
Figure 6G:
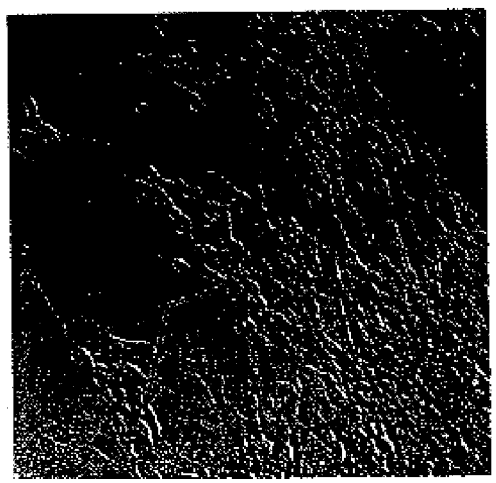

The data reported herein shows the ability of CLN to block the activity of cells treated with 20 μM retinoic acid (the toxicity developed too rapidly in cells treated with 40 μM). Table 1C indicates that 1.0 μg/ml of CLN almost completely blocked the cytotoxicity of retinoic acid. The retinoic acid induced differentiation in these cells by day two, but the cells started showing signs of toxicity by day 6. CLN, 1.0 μg/ml, added on day one or for 30 minutes on day five of the experiment completely blocked the toxicity, and similar to the finding with Beta-amyloid, also induced the cells to proliferate. FIGS. 6F and 6G further document the finding. FIG. 6F shows the toxicity induced by retinoic acid compared 10 FIG. 6G, which clearly shows differentiated cells (see legends).

Colostrinin inhibited the eventual development of cytotoxicity by Retinoic Acid when added at the same time or 5 days later. Colostrinin added at Day 1 also inhibited the development of toxicity by β-Amyloid added on Day 5 and was dose dependent (data not shown).

The ability of CLN to inhibit apoptotic effects of two substances, Beta-amyloid and retinoic acid, indicates it may have potential biological use in many areas where apoptosis plays a role, e.g., virus infections, chronic diseases and attempts to get stem cells to grow and differentiate, among many others.

Table 1. Differentiating, Anti-Apoptotic and Protective Activity of Colostrinin Against β-Amyloid and Retinoic Acid in Neuronal Derived SH-SY5Y Cells

TABLE 1

Differentiating, Anti-Apoptotic and Protective Activity of Colostrinin Against β-Amyloid and Retinoic Acid in Neuronal Derived SH-SY5Y Cells

| TREATMENT | DOSE COLOSTRININ (MG/ML) | TOXICITY | DIFFERENTI-ATION |
|---|---|---|---|
| A. Differentiating Activity | | | |
| | 3.0 (Day 5)[a] | − (Day 8)[b] | ++++ (Day 8)[b] |
| | 1.0 (Day 5)[a] | − (Day 8)[b] | ++++ (Day 8)[b] |
| | 0.1 (Day 5)[a] | − (Day 8)[b] | +++ (Day 8)[b] |
| | 0.01 (Day 5)[a] | +/− (Day 8)[b] | ++ (Day 8)[b] |
| B. Anti-apoptotic Activity | | | |
| β-Amyloid 10 μg/ml (Day 5)[a] | | +++ (Day 8)[b] | − (Day 8)[b] |
| β-Amyloid 10 μg/ml (Day 5)[a] | 3.0 (Day 5)[a] | − (Day 8)[b] | +++ (Day 8)[b] |
| β-Amyloid 10 μg/ml (Day 5)[a] | 1.0 (Day 5)[a] | +/− (Day 8)[b] | +++ (Day 8)[b] |
| β-Amyloid 10 μg/ml (Day 5)[a] | 0.1 (Day 5)[a] | +/− (Day 8)[b] | ++ (Day 8)[b] |
| β-Amyloid 10 μg/ml (Day 5)[a] | 0.01 (Day 5)[a] | + (Day 8)[b] | + (Day 8)[b] |
| C. Protection Against Retinoic Acid Activity | | | |
| Retinoic Acid 20 μM (Day 1)[a] | | − (Day 2)[b] | ++++ (Day 2)[b] |
| Retinoic Acid 20 μM (Day 1)[a] | | +++ (Day 8)[b] | + (Day 8)[b] |
| Retinoic Acid 20 μM (Day 1)[a] | 1.0 (Day 5)[a] | − (Day 8)[b] | ++++ (Day 8)[b] |
| Retinoic Acid 20 μM (Day 1)[a] | 1.0 (Day 1)[a] | + (Day 8)[b] | ++++ (Day 8)[b] |

TABLE 1-continued

Differentiating, Anti-Apoptotic and Protective Activity of Colostrinin Against β-Amyloid and Retinoic Acid in Neuronal Derived SH-SY5Y Cells

| TREATMENT | DOSE COLOSTRININ (MG/ML) | TOXICITY | DIFFERENTI-ATION |
|---|---|---|---|
| D. Control | | | |
| Mock Treated (Day 1)[a] | | − (Day 5 & 8)[b] | − (Day 5 & 8)[b] |

++++ Approximately 100% of the cells
+ Approximately 25% of the cells
[a]Day of treatment
[b]Day cells observed Example 7

Inhibition of 4HNE-Induced Apoptosis by CLN

Apoptosis is a specific mode of cell death recognized by a characteristic pattern of morphological, biochemical, and molecular changes. Currently the hallmark of apoptosis in vitro is DNA fragmentation and changes in plasma membrane reorganization that allows for the surface expression of phosphatidyl-D-serine and result in increased membrane permeability. The protection of cells against 4HNE by CLN using increased permeability and cell membrane expression of phosphatidyl-D-serine was investigated.

Cells were simultaneously labeled with fluorochrome-conjugated annexin V-PE (detecting PS asymmetry in the plasma membrane, an early marker of apoptosis), 7-aminoactinomycin D (7-AAD) (detecting increased membrane permeability associated with both apoptosis and necrosis). A dual laser flow cytometer (either a Becton-Dickinson FACScan) was used for the simultaneous detection of the PE-conjugated annexin V (which is excited at 632 nm and emits at 660 nm), 7-AAD (excited at 488 nm and emitting at 670 nm). Fluorochrome compatibility was excellent, although careful intralaser compensation is required for simultaneous use of PE and 7-AAD.

Figure 7A:
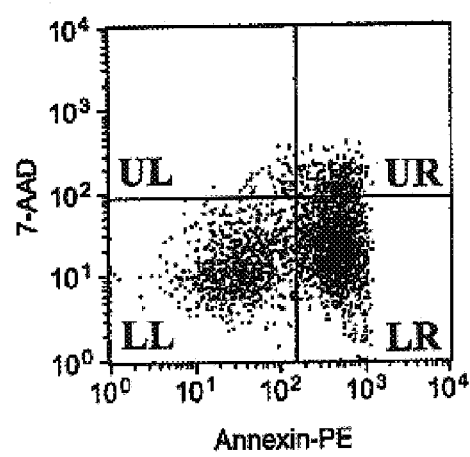
FIG. 7. Analysis of apoptosis by flow cytometry. (A) Induction of apoptosis by 4HNE (100 nM). UL, upper left; UR, upper right: necrotic cells; LL, lower left: viable cells; LR, lower right: apoptotic cells. (B) Absence of apoptosis in mock-treated cells. UL, upper left; UR, upper right: necrotic cells; LL, lower left: viable cells; LR, lower right: apoptotic cells.
Figure 7B:
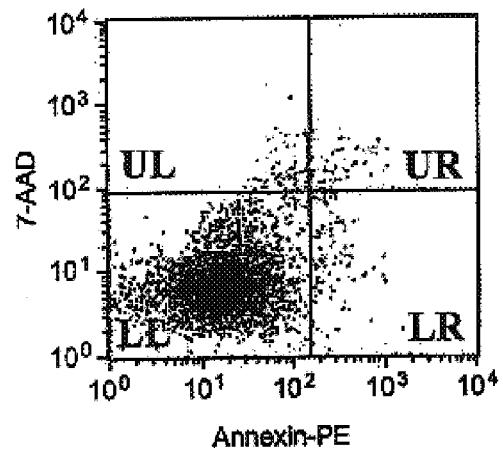
Figure 8:
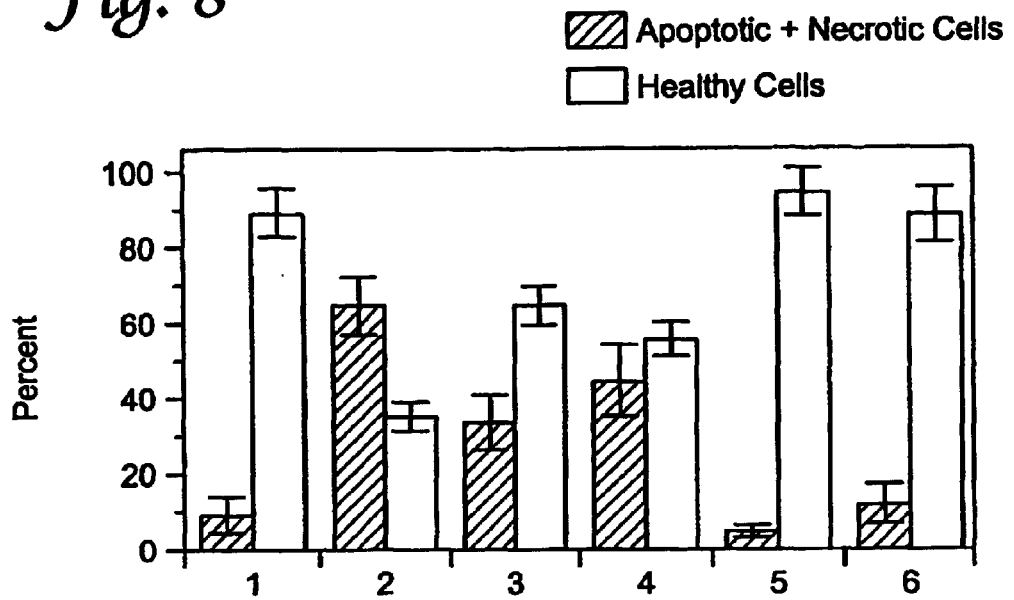
FIG. 8. Inhibition of 4HNE-induced apoptosis by CLN. PC12 cells were treated with CLN (1 μg per ml) for 15 min and 4HNE (100 nM) was added. Twenty four hours later, cells were harvested and stained with annexin V-PE and 7-AAD. 1, solvent alone; 2, 100 nM 4HNE; 3, TROLOX (vitamin E) 4, col (internal control)+100 nM 4HNE; 5, CLN alone (1 μg per ml); 6, CLN (1 μg per ml)+100 nM 4HNE.

The analysis of apoptosis by flow cytometry is shown in FIG. 7. The results of the inhibition of 4HNE-induced apoptosis by CLN are shown in FIG. 8.

Example 8

Inhibition of UV-Irradiation-Induced Apoptosis by CLN

Chronic repeated UV exposures are the primary cause of benign and malignant skin tumors, including malignant melanoma In experimental animal models, among types of solar radiation, ultraviolet B (290–320 mm) radiation is highly mutagenic and carcinogenic compare to ultraviolet A (320–400 nm) radiation. Based on current understanding of DNA damage caused by direct UV radiation and by indirect stress via reactive oxygen species and DNA repair mechanisms are responsible for UV irradiation-induced skin tumor development in human cells.

UVB exposure leads to a time-dependent increase in the production of intracellular peroxide and superoxide anions and may induce carcinogenic mutations and apoptosis. Besides being a major cause of oxidative stress in the cells, UVB-irradiation induces apoptosis by a large number of unrelated pathways such as enhanced Fas transcription and/ or mRNA stability, induction of transcriptional factors viz c-fos, c-jun, SAP-1 and nuclear factor kB gene expression. A possible prevention of UV-induced skin cancer by feeding or topical use of antioxidants, such as polyphenols, and vitamins are observed.

Figure 9:
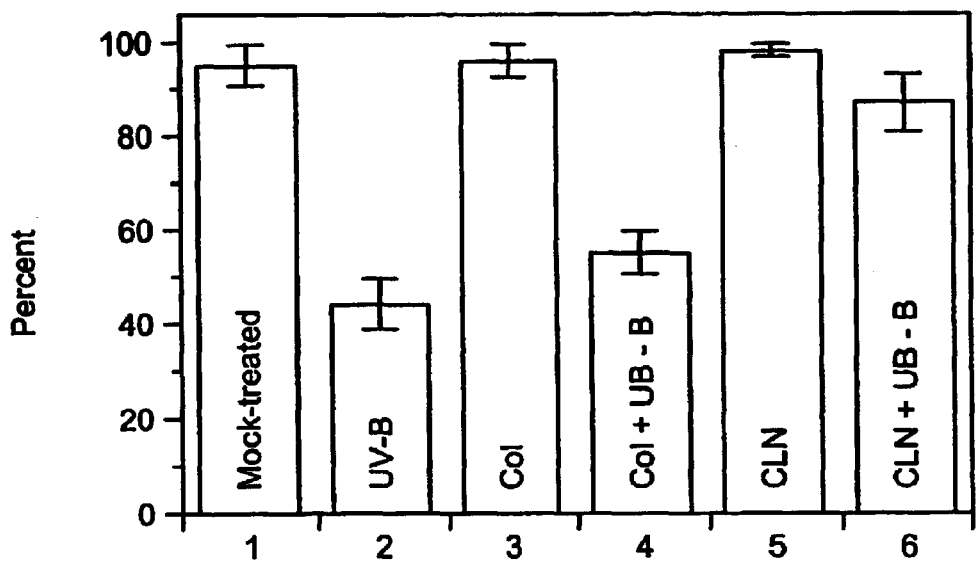
FIG. 9. Inhibition of UV-B-induced apoptosis by CLN. Parallel cultures of PC12 cells were treated with CLN (1 μg per ml) or col (1 μg per ml) and exposed to LD50 of UV-B. Twenty four hours later, cells were harvested and stained with annexin V-PE and 7-AAD. 1, Mock-treated; 2, UV-B (LD50); 3, col (internal control); 4, col+UV-B (LD50); 5, CLN alone (1 μg per ml); 6, CLN (1 μg per ml)+UV-B (LD50).

The effect of CLN on ultraviolet B (UVB)-induced apoptosis and DNA damage in cultured PC12 cells has been determined. The apoptosis was determined by flow cytometry. The comet assay was employed to detect DNA damage in individual cell. The results shown in FIG. 9 indicate an inhibitory effect of CLN on UVB-induced apoptosis. CLN-treated cells also showed a significantly reduced DNA damage. Semi-confluent cells with >98% viability (tested with trypan blue dye exclusion) were used in all experiments. PC12 cells were exposed to UV-B irradiation. Lethal dose 50 (LD50) was determined in preliminary studies. Cells were irradiated by a dose result in 50% cell death.

CONCLUSION

Taken together, these results show that CLN can be involved in regulation of the cellular redox status, GSH metabolism, and modulation of ROS-induced signaling-mediated down-stream events (e.g., JNK, p53). These results further suggest a potential mechanism(s) by which CLN could modulate a network, resulting in cytokine, chemokine production, cell differentiation and may explain it's beneficial effects on pathogenic processes involved in AD and other chronic neuro-degenerative diseases.

Although the invention has been disclosed with reference to its preferred embodiments, from reading this description those of skill in the art may appreciate changes and modification that may be made which do not depart from the scope and spirit of the invention as described above and claimed hereafter. All references, patents, and patent applications cited herein are incorporated herein by reference in their entirety as if individually incorporated.

Sequence Listing Free Text

The following are all synthetic peptide sequences.

| SEQ ID NO:1 | MQPPPLP |
| SEQ ID NO:2 | LQTPQPLLQVMMEPQGD |
| SEQ ID NO:3 | DQPPDVEKPDLQPFQVQS |
| SEQ ID NO:4 | LFFFLPVVNVLP |
| SEQ ID NO:5 | DLEMPVLPVEPFPFV |
| SEQ ID NO:6 | MPQNFYKLPQM |
| SEQ ID NO:7 | VLEMKFPPPPQETVT |
| SEQ ID NO:8 | LKPFPKLKVEVFPFP |
| SEQ ID NO:9 | VVMEV |
| SEQ ID NO:10 | SEQP |
| SEQ ID NO:11 | DKE |
| SEQ ID NO:12 | FPPPK |
| SEQ ID NO:13 | DSQPPV |
| SEQ ID NO:14 | DPPPPQS |
| SEQ ID NO:15 | SEEMP |
| SEQ ID NO:16 | KYKLQPE |
| SEQ ID NO:17 | VLPPNVG |
| SEQ ID NO:18 | VYPFTGPIPN |
| SEQ ID NO:19 | SLPQNILPL |
| SEQ ID NO:20 | TQTPVVVPPF |
| SEQ ID NO:21 | LQPEIMGVPKVKETMVPK |
| SEQ ID NO:22 | HKEMPFPKYPVEPFTESQ |
| SEQ ID NO:23 | SLTLTDVEKLHLPLPLVQ |
| SEQ ID NO:24 | SWMHQPP |
| SEQ ID NO:25 | QPLPPTVMFP |
| SEQ ID NO:26 | PQSVLS |
| SEQ ID NO:27 | LSQPKVLPVPQKAVPQRDMPIQ |
| SEQ ID NO:28 | AFLLYQE |
| SEQ ID NO:29 | RGPFPILV |
| SEQ ID NO:30 | ATFNRYQDDHGEEILKSL |
| SEQ ID NO:31 | VESYVPLFP |
| SEQ ID NO:32 | FLLYQEPVLGPVR |
| SEQ ID NO:33 | LNF |
| SEQ ID NO:34 | MHQPPQPLPPTVMFP |

SEQUENCE LISTING

```
<160> NUMBER OF SEQ ID NOS:  34

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 1

Met Gln Pro Pro Pro Leu Pro
 1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 2

Leu Gln Thr Pro Gln Pro Leu Leu Gln Val Met Met Glu Pro Gln Gly
 1               5                  10                  15
```

Asp

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Asp Gln Pro Pro Asp Val Glu Lys Pro Asp Leu Gln Pro Phe Gln Val
 1               5                  10                  15

Gln Ser

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Leu Phe Phe Phe Leu Pro Val Val Asn Val Leu Pro
 1               5                  10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Asp Leu Glu Met Pro Val Leu Pro Val Glu Pro Phe Pro Phe Val
 1               5                  10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Met Pro Gln Asn Phe Tyr Lys Leu Pro Gln Met
 1               5                  10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Val Leu Glu Met Lys Phe Pro Pro Pro Gln Glu Thr Val Thr
 1               5                  10                  15

<210> SEQ ID NO 8
<211> LENGTH: 15
<212> TYPE: PRT
<213> ORGANISM: Artificial Sequence

```
<220> FEATURE:
<223> OTHER INFORMATION: Description of Artificial Sequence:  synthetic
      peptide

<400> SEQUENCE: 8

Leu Lys Pro Phe Pro Lys Leu Lys Val Glu Val Phe Pro Phe Pro
 1               5                  10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 9

Val Val Met Glu Val
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 10

Ser Glu Gln Pro
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 11

Asp Lys Glu
 1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 12

Phe Pro Pro Pro Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 13

Asp Ser Gln Pro Pro Val
 1               5
```

```
<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Asp Pro Pro Pro Pro Gln Ser
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Ser Glu Glu Met Pro
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Lys Tyr Lys Leu Gln Pro Glu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Val Leu Pro Pro Asn Val Gly
 1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Val Tyr Pro Phe Thr Gly Pro Ile Pro Asn
 1               5                  10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 19

Ser Leu Pro Gln Asn Ile Leu Pro Leu
  1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 20

Thr Gln Thr Pro Val Val Val Pro Pro Phe
  1               5                  10

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 21

Leu Gln Pro Glu Ile Met Gly Val Pro Lys Val Lys Glu Thr Met Val
  1               5                  10                  15

Pro Lys

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 22

His Lys Glu Met Pro Phe Pro Lys Tyr Pro Val Glu Pro Phe Thr Glu
  1               5                  10                  15

Ser Gln

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 23

Ser Leu Thr Leu Thr Asp Val Glu Lys Leu His Leu Pro Leu Pro Leu
  1               5                  10                  15

Val Gln

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 24

Ser Trp Met His Gln Pro Pro
```

```
                                 1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 25

Gln Pro Leu Pro Pro Thr Val Met Phe Pro
 1               5                  10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 26

Pro Gln Ser Val Leu Ser
 1               5

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 27

Leu Ser Gln Pro Lys Val Leu Pro Val Pro Gln Lys Ala Val Pro Gln
 1               5                  10                  15

Arg Asp Met Pro Ile Gln
            20

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 28

Ala Phe Leu Leu Tyr Gln Glu
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 29

Arg Gly Pro Phe Pro Ile Leu Val
 1               5

<210> SEQ ID NO 30
<211> LENGTH: 18
<212> TYPE: PRT
```

-continued

```
<213> ORGANISM: Artificial Sequence
<220> FEATURE:
<223> OTHER INFORMATION: Description of Artificial Sequence:  synthetic
      peptide

<400> SEQUENCE: 30

Ala Thr Phe Asn Arg Tyr Gln Asp Asp His Gly Glu Glu Ile Leu Lys
 1               5                  10                  15

Ser Leu

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 31

Val Glu Ser Tyr Val Pro Leu Phe Pro
 1               5

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 32

Phe Leu Leu Tyr Gln Glu Pro Val Leu Gly Pro Val Arg
 1               5                  10

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 33

Leu Asn Phe
 1

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 34

Met His Gln Pro Pro Gln Pro Leu Pro Pro Thr Val Met Phe Pro
 1               5                  10                  15
```

What is claimed is:

1. A method for inducing a cytokine in a cell, the method comprising contacting the cell with an immunological regulator under conditions effective to induce a cytokine, wherein the immunological regulator is selected from the group consisting of a constituent peptide of colostrinin, an active analog thereof, and combinations thereof;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCK-VEVFPFP (SEQ ID NO:8), and MHQPPQ-PLPPTVMFP (SEQ ID NO:34); and wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34) and wherein said active analog induces a cytokine.

2. The method of claim 1 wherein the cell is present in a cell culture, a tissue, an organ, or an organism.

3. The method of claim 1 wherein the cell is a mammalian cell.

4. The method of claim 3 wherein the cell is a human cell.

5. The method of claim 1 wherein the immunological regulator is the colostrinin constituent peptide MQPPPLP (SEQ ID NO: 1), an active analog thereof, or a combination thereof.

6. A method for modulating an immune response in a cell, the method comprising contacting the cell with an immunological regulator under conditions effective to induce a cytokine, wherein the immunological regulator is selected from the group consisting of a constituent peptide of colostrinin, an active analog thereof, and combinations thereof;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34); and wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34) and wherein said active analog modulates an immune response.

7. The method of claim 6 wherein the cell is present in a cell culture, a tissue, an organ, or an organism.

8. The method of claim 6 wherein the cell is a mammalian cell.

9. The method of claim 8 wherein the cell is a human cell.

10. The method of claim 6 wherein the immunological regulator is the colostrinin constituent peptide MQPPPLP (SEQ ID NO: 1), an active analog thereof, or a combination thereof.

11. A method for modulating an immune response in a patient, the method comprising administering to the patient an immunological regulator under conditions effective to induce a cytokine, wherein the immunological regulator is selected from the group consisting of a constituent peptide of colostrinin, an active analog thereof, and combinations thereof;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34); and wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34) and wherein said active analog modulates an immune response.

12. The method of claim 11 wherein the immunological regulator is administered as part of a dietary supplement.

13. The method of claim 11 wherein the immunological regulator is administered topically.

14. The method of claim 11 wherein the patient is an animal.

15. The method of claim 14 wherein the patient is a human.

16. The method of claim 11 wherein the immune response is a specific immune response.

17. The method of claim 11 wherein the immune response is a nonspecific immune response.

18. The method of claim 11 wherein the immune response is the interferon response or antibody production.

19. The method of claim 11 wherein the immunological regulator is the colostrinin constituent peptide MQPPPLP (SEQ ID NO: 1), an active analog thereof, or a combination thereof.

20. A method for modulating leukocyte proliferation, the method comprising contacting leukocytes with a leukocyte regulator selected from the group consisting of colostrinin, a constituent peptide thereof, an active analog thereof, and combinations thereof, under conditions effective to change the number of leukocytes, wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34);

wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34);

and wherein the number of leukocytes is changed.

21. The method of claim 20 wherein the leukocytes are present in a cell culture or an organism.

22. The method of claim 20 wherein the leukocytes are mammalian cells.

23. The method of claim 22 wherein the leukocytes are human cells.

24. The method of claim 20 wherein the leukocytes are increased in number.

25. The method of claim 24 wherein the leukocytes are differentiated.

26. The method of claim 20 wherein the leukocyte regulator is a constituent peptide of colostrinin.

27. The method of claim 20 wherein the leukocyte regulator is the colostrinin constituent peptide VESYVPLFP (SEQ ID NO:31), an active analog thereof, or a combination thereof.

28. The method of claim 20 wherein the leukocyte regulator is the colostrinin constituent peptide MQPPPLP (SEQ ID NO:1), an active analog thereof, or a combination thereof.

29. A method for modulating leukocyte proliferation in a patient, the method comprising administering to the patient a leukocyte regulator selected from the group consisting of colostrinin, a constituent peptide thereof, an active analog thereof, and combinations thereof, under conditions effective to change the number of leukocytes;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCK-VEVFPFP (SEQ ID NO:8), VESYVPLFP (SEQ ID NO:31), and MHQPPQPLPPTVMFP (SEQ ID NO:34);

wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCK-VEVFPFP (SEQ ID NO:8), VESYVPLFP (SEQ ID NO:31), and MHQPPQPLPPTVMFP (SEQ ID NO:34), and wherein the number of leukocytes is changed.

30. The method of claim 29 wherein the patient is a human.

31. The method of claim 29 wherein the leukocytes are increased in number.

32. The method of claim 31 wherein the leukocytes are differentiated.

33. The method of claim 29 wherein the leukocyte regulator is a constituent peptide of colostrinin.

34. The method of claim 29 wherein the leukocyte regulator is the colostrinin constituent peptide VESYVPLFP (SEQ ID NO:31), an active analog thereof, or a combination thereof.

35. The method of claim 29 wherein the leukocyte regulator is the colostrinin constituent peptide MQPPPLP (SEQ ID NO:1), an active analog thereof, or a combination thereof.

36. The method of claim 29 wherein the leukocyte regulator is administered as part of a dietary supplement.

37. The method of claim 29 wherein the leukocyte regulator is administered topically.

* * * * *

UNITED STATES PATENT AND TRADEMARK OFFICE
CERTIFICATE OF CORRECTION

PATENT NO. : 6,903,068 B1
APPLICATION NO. : 09/641801
DATED : June 7, 2005
INVENTOR(S) : G. John Stanton et al.

It is certified that error appears in the above-identified patent and that said Letters Patent is hereby corrected as shown below:

Delete the title page and substitute therefore the attached title page.

Delete Columns 1-36 and substitute therefore the attached Columns 1-36.

Signed and Sealed this

Nineteenth Day of August, 2008

JON W. DUDAS
*Director of the United States Patent and Trademark Office*

(12) United States Patent
Stanton et al.

(10) Patent No.: US 6,903,068 B1
(45) Date of Patent: *Jun. 7, 2005

(54) USE OF COLOSTRININ, CONSTITUENT PEPTIDES THEREOF, AND ANALOGS THEREOF FOR INDUCING CYTOKINES

(75) Inventors: G. John Stanton, Texas City, TX (US); Thomas K. Hughes, Jr., Galveston, TX (US); Istvan Boldogh, Galveston, TX (US); Jerzy A. Georgiades, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 488 days.

This patent is subject to a terminal disclaimer.

(21) Appl. No.: 09/641,801

(22) Filed: Aug. 17, 2000

Related U.S. Application Data

(60) Provisional application No. 60/149,311, filed on Aug. 17, 1999.

(51) Int. Cl.[7] ............... A61K 38/00; A61K 38/02; A61K 38/08; A61K 38/18

(52) U.S. Cl. ............... 514/2; 514/12; 514/13; 514/14; 514/15; 514/16; 514/17; 530/300; 530/324; 530/326; 530/327; 530/328; 530/329

(58) Field of Search ............... 514/2, 12, 13, 14, 514/15, 16, 17, 18; 530/300, 324, 326, 327, 530/328, 329, 350, 334; 424/85.1, 535

(56) References Cited

U.S. PATENT DOCUMENTS

| | | | |
|---|---|---|---|
| 4,938,949 A | 7/1990 | Borch et al. | |
| 5,595,887 A | 1/1997 | Coolidge et al. | |
| 6,040,180 A | 3/2000 | Johe | |
| 6,410,058 B2 * | 6/2002 | Gohlke et al. | 424/535 |
| 6,500,798 B1 * | 12/2002 | Stanton et al. | 514/2 |
| 2003/0091606 A1 | 5/2003 | Stanton et al. | |

FOREIGN PATENT DOCUMENTS

| | | |
|---|---|---|
| JP | 06 041191 A | 2/1994 |
| WO | WO 95/00155 | 1/1995 |
| WO | WO 95/30686 | 11/1995 |
| WO | WO 98/14473 * | 4/1998 |
| WO | WO 99/65329 | 12/1999 |
| WO | WO 00/75173 | 12/2000 |
| WO | WO 01/11937 | 2/2001 |
| WO | WO 01/12650 | 2/2001 |
| WO | WO 01/12651 | 2/2001 |
| WO | WO 02/13849 | 2/2002 |
| WO | WO 02/13850 | 2/2002 |
| WO | WO 02/13851 | 2/2002 |
| WO | WO 03/33423 | 10/2003 |

OTHER PUBLICATIONS

Kruzel et al. (Dec. 2001) "Towards an Understanding of Biological Role of Colonstrinin Peptides," Journal of Molecular Neuroscience 17(3): 379–389.*

Inglot, Junsz, and Lisowski Colostrinine:a Proline–Rich Polypeptide from Ovine Colostrum Is a Modest Cytokine Inducer in Human Leukocytes, 1996, Archivum Immunologiae et Therapiae Experimentalis (44) 215–224.*

Elgert, "Immunology: Understanding the Immune System" Text (1996) Wiley–Liss 1st Ed. pp. 24–26 and 199–217.*

Ngo et al. Computational Complexity, Protein Structure Prediction, and the Levinthal Paradox (1994) The Protein Folding Problem and Teriary Structure Prediction (#14), 491–495.*

Wells Addivity of Mutational Effects in Proteins (1990) Biochemistry (29): 37, 8509–8517.*

Babbit, ed., *The Vanderbilt Rubber Handbook*, R.T. Vanderbilt Company, Inc., Norwalk, CT, pp. 344–397 (1978).

Bespalov et al., "Fabs specific for 8–oxoguanine: control of DNA binding," *J Mol Biol.* Nov. 12, 1999;293(5):1085–95.

Blach–Olszewska et al., "Stimulatory effect of ovine colostrinine (a proline–rich polypeptide) on interferons and tumor necrosis factor production by murine resident peritoneal cells," *Arch Immunol Ther Exp (Warsz).* 1997; 45(1):43–7.

Buescher et al., "Clostral antioxidants: separation and characterization of two activities in human colostrum," *J Pediatr Gastroenterol Nutr1.* Jan. 1992; 14(1):47–56.

Calingasan et al., "Protein–bound acrolein: a novel marker of oxidative stress in Alzheimer's disease," *J. Neurochem.* Feb. 1999;72(2):751–6.

Chao "Growth factor signaling: where is the specificity?" *Cell.* Mar. 20, 1992; 68(6):995–7.

Esterbauer et al., "Chemistry and biochemistry of 4–hydroxynonenal, malonaldehyde and related aldehydes," *Free Radic Biol Med.* 1991;11(1):81–128.

Fields et al., *Synthetic Peptides: A User's Guide*, W.M. Freeman & Company, New York, NY, pp. 77–183 (1992).

Fillmore et al., "Differentiation of PC12 cells with nerve growth factor is associated with induction of transin synthesis and release," *J Neurosci Res.* Apr. 1992;31(4):662–9.

Gabbita et al., "Increased nuclear DNA oxidation in the brain in Alzheimer's disease," *J Neurochem.* Nov. 1998;71(5):2034–40.

Gabbita et al., "Decrease in peptide methionine sulfoxide reductase in Alzheimer's disease brain," *J Neurochem.* Oct. 1999;73(4):1660–6.

(Continued)

*Primary Examiner*—Elizabeth C. Kemmerer
*Assistant Examiner*—Christopher James Nichols
(74) *Attorney, Agent, or Firm*—Mueting, Raasch & Gebhardt, P.A.

(57) ABSTRACT

The present invention discloses a use of colostrinin, a constituent peptide thereof, and/or an analog thereof as an immunological regulator and as a blood cell regulator in animals including humans.

37 Claims, No Drawings

OTHER PUBLICATIONS

Good et al., "Evidence of neuronal oxidative damage in Alzheimer's disease," *Am J Pathol.* Jul. 1996;149(1):21–8.

Gratama et al., "Flow cytometric quantitation of immunofluorescence intensity: problems and perspectives. European Working Group on Clinical Cell Analysis," *Cytometry,* Oct. 1, 1998;33(2):166–78.

Grunwald et al., "In situ analysis of chromatin proteins during development and cell differentiation using flow cytometry," *Methods Mol Biol.* 1999;119:443–54.

Hensley et al., "Brain regional correspondence between Alzheimer's disease histopathology and biomarkers of protein oxidation," *J Neurochem.* Nov. 1995; 65(5):2146–56.

Hughes et al., "Modulation of immune responses by anabolic androgenic steroids," *Int J Immunopharmacol.* Nov. 1995;17(11):857–63.

Inglot et al., "Colostrinine: a proline-rich polypeptide from ovine colostrum is a modest cytokine inducer in human leukocytes," *Arch Immunol Ther Exp (Warsz).* 1996;44(4):215–24.

Inglot et al., "Colostrinin for treatment of Alzheimer's disease," *European Cytokine Network.* Sep. 1996;7(3):458(abstract 51).

Inglot et al., "Tumor-associated antigens are cytokine inducers and hyporeactivity factors to the immune system," *Biotherapy.* 1998;11(1):27–37.

Janusz et al., "Isolation and characterization of a proline-rich polypeptide from ovine colostrum," *FEBS Lett.* Dec. 15, 1974;49(2):276–9.

Janusz et al., "Chemical and physical characterization of a proline-rich polypeptide from sheep colostrum," *Biochem J.* Oct. 1, 1981;199(1):9–15.

Janusz et al., "Proline-rich polypeptide (PRP)—an immunomodulatory peptide from ovine colostrum," *Arch Immunol Ther Exp (Warsz).* 1993;41(5–6):275–9.

Kim et al., "Simultaneous differentiation and quantitation of erythroblasts and white blood cells on a high throughput clinical haematology analyser," *Clin Lab Haematol.* Feb. 1998;20(1):21–9.

Kooy et al., "Oxidation of 2',7'-dichlorofluorescin by peroxynitrite," *Free Radic Res.* Sep. 1997;27(3):245–54.

LeBel et al., "Evaluation of the probe 2',7'-dichlorofluorescin as an indicator of reactive oxygen species formation and oxidative stress," *Chem Res Toxicol.* Mar.–Apr. 1992;5(2):227–31.

Leszek et al., "Colostrinin: a proline-rich polypeptide (PRP) complex isolated from ovine colostrum for treatment of Alzheimer's disease. A double-blind, placebo-controlled study," *Arch Immunol Ther Exp (Warsz),* 1999;47(6):377–85.

Levi et al., "The mode of action of nerve growth factor in PC12 cells," *Mol Neurobiol.* 1988 Fall;2(3):201–26.

Lovell et al., "Elevated thiobarbituric acid-reactive substances and antioxidant enzyme activity in the brain in Alzheimer's disease," *Neurology.* Aug. 1995; 45(8):1594–601.

Lovell et al., "Elevated 4-hydroxynonenal in ventricular fluid in Alzheimer's disease," *Neurobiol Aging.* Sep.–Oct. 1997;18(5):457–61.

Lovell et al., "Decreased glutathione transferase activity in brain and ventricular fluid in Alzheimer's disease," *Neurology.* Dec. 1998;51(6):1562–6.

Lovell et al., "Increased DNA oxidation and decreased levels of repair products in Alzheimer's disease ventricular CSF," *J Neurochem.* Feb. 1999;72(2):771–6.

Lovell et al., "Decreased base excision repair and increased helicase activity in Alzheimer's disease brain," *Brain Res.* Feb. 7, 2000;855(1):116–23.

Markesberry, "Oxidative stress hypothesis in Alzheimer's disease," *Free Radic Biol Med.* 1997;23(1):134–47.

Markesbery et al., "Four-hydroxynonenal, a product of lipid peroxidation, is increased in the brain in Alzheimer's disease," *Neurobiol Aging.* Jan.–Feb. 1998;19(1):33–6.

Markesbery et al. "Oxidative alterations in Alzheimer's disease," *Brain Pathol.* Jan. 1999;9(1):133–46.

Marshall et al., "Specificity of receptor tyrosine kinase signaling: transient versus sustained extracellular signal-regulated kinase activation," *Cell,* Jan. 1995 27:80(2):179–85.

McHeyzer-Williams et al., "Enumeration and characterization of memory cells in the TH compartment," *Immunol Rev.* Apr. 1996;150:5–21.

Mecocci et al., "Oxidative damage to mitochondrial DNA is increased in Alzheimer's disease," *Ann Neurol.* Nov. 1994;36(5):747–51.

Mishell et al., *Selected Methods in Cellular Immunology,* W.H. Freeman, San Francisco, CA; title page and table of contents only, 9 pages (1980).

Montine et al., "Cerebrospinal fluid F2-isoprostane levels are increased in Alzheimer's disease," *Ann Neurol.* Sep. 1998;44(3):410–3.

Ostrea et al., "Influence of breast-feeding on the restoration of the low serum concentration of vitamin E and beta-carotene in the newborn infant," *Am J Obstet Gynecol.* May 1986;154(5):1014–7.

Peunova et al., "Nitric oxide triggers a switch to growth arrest during differentiation of neuronal cells," *Nature.* May 4, 1995;375(6526):68–73.

Piasecki et al., "Coincidence between spontaneous release of interferon and tumor necrosis factor by colostral leukocytes and the production of a colostrinine by human mammary gland after normal delivery," *Arch Immunol Ther Exp (Warsz),* 1997;45(1):109–17.

Popik et al., "Colostrinin, a polypeptide isolated from early milk, facilitates learning and memory in rats," *Pharmacol Biochem Behav.* Sep. 1999;64(1):183–9.

Prasad et al., "Regional membrane phospholipid alterations in Alzheimer's disease," *Neurochem Res.* Jan. 1998;23(1)81–8.

Roberts II et al., "Formation of isoprostane-like compounds (neuroprostanes) in vivo from docosahexaenoic acid," *J Biol Chem.* May 29, 1998;273(22):13605–12.

Rothe et al., "Flow cytometric analysis of respiratory burst activity in phagocytes with hydroethidine and 2',7'-dichlorofluorescin," *J Leukoc Biol.* May 1990; 47(5):440–8.

Royall et al., "Evaluation of 2',7'-dichlorofluorescin and dihydrorhodamine 123 as fluorescent probes for intracellular $H_2O_2$ in cultured endothelial cells," *Arch Biochem Biophys.* May 1993;302(2):348–55.

Subbarao et al., "Autopsy samples of Alzheimer's cortex show increased peroxidation in vitro," *J Neurochem.* Jul. 1990;55(1):342–5.

Schacter et al., "Differential susceptibility of plasma proteins to oxidative modification: examination by western blot immunoassay," *Free Radic Biol Med.* Nov. 1994;17(5):429–37.

Singh et al., "Dietary intake, plasma levels of antioxidant vitamins, and oxidative stress in relation to coronary artery disease in elderly subjects," *Am J Cardiol.* Dec. 15, 1995;76(17):1233–8.

Smith et al., "Advanced Maillard reaction end products are associated with Alzheimer disease pathology," *Proc Natl Acad Sci U S A.* Jun. 7, 1994; 91(12):5710–4.

Smith et al., "Oxidative damage in Alzheimer's," *Nature.* Jul. 11, 1996; 382(6587):120–1.

Smith et al., "Excess brain protein oxidation and enzyme dysfunction in normal aging and in Alzheimer's disease," *Proc Natl Acad Sci U S A.* Dec. 1, 1991; 88(23):10540–3.

Svennerholm et al., "Membrane lipids, selectively diminished in Alzheimer brains, suggest synapse loss as a primary event in early-onset form (type I) and demyelination in late-onset form (type II)," *J Neurochem.* Mar. 1994; 62(3):1039–47.

Takahashi et al., "Spontaneous transformation and immortalization of human endothelial cells," *In Vitro Cell Dev Biol.* Mar. 1990;26(3 Pt 1):265–74.

Tsuchiya et al., "In vivo visualization of oxygen radical-dependent photoemission," *Methods Enzymol (Oxygen Radicals in Biological Systems).* 1994;233C:128–40.

Villas et al., "Flow cytometry: an overview," *Cell Vis.* Jan.–Feb. 1998;5(1):56–61.

Yan et al., "Glycated tau protein in Alzheimer disease: a mechanism for induction of oxidant stress," *Proc Natl Acad Sci U S A.* Aug. 2, 1994;91(16):7787–91.

Zimecki et al., "Effect of a proline-rich polypeptide (PRP) on the development of hemolytic anemia and survival of New Zealand black (NZB) mice," *Arch Immunol Ther Exp (Warsz).* 1991;39(5–6):461–7.

Altin et al., "Differential Induction of Primary-response (TIS) Genes in PC12 Pheochromocytoma Cells and the Unresponsive Variant PC12nnr5," *Journal of Biological Chemistry,* Mar. 25, 1991;266(9): 5401–5406.

Anneren et al., "GTK, a Src-related Tyrosine Kinase, Induces Nerve Growth Factor-independent Neurite Outgrowth in PC 12 Cells through Activation of the Rap1 Pathway," *Journal of Biological Chemistry,* Sep. 15, 2000;275(37): 29153–29161.

Bagchi et al., "Comparative in vitro and in vivo protein kinase C activation by selected pesticides and transition metal salts," *Toxicology Letters,* 1997;91: 31–37.

Bikfalvi et al., "Biological Roles of Fibroblast Growth Factor-2," *Endocrine Reviews,* Feb. 1997;18(1):26–45.

Chen et al., "Lithium Increase Tyrosine Hydroxylase Levels both In Vivo and In Vitro," *Journal of Neurochemistry,* 1998;70(4): 1768–1771.

Cui et al., "Effect of Nucleoside Analogs on Neurite Regeneration and Mitochondrial DNA Synthesis in PC-12 Cells," *Journal of Pharmacology and Experimental Therapeutics,* 1997;280(3): 1228–1234.

Dage et al., "NS 1231, a novel compound with neurotrophic-like effects in vitro and in vivo," *Journal of Neurochemistry,* 2002;81: 17–24.

DeJongh et al., "Estimation of Systemic Toxicity of Acrylamide by Integration of in vitro Toxicity Data with Kinetic Simulations," *Toxicology and Applied Pharmacology,* 1999;158: 261–268.

Doye et al., "Phosphorylation of Stathmin and Other Proteins Related to Nerve Growth Factor-induced Regulation of PC12 Cells," *Journal of Biological Chemistry,* Jul. 15, 1990;265(20): 11650–11655.

Feng et al., "NF-κB/Rel Proteins are Required for Neuronal Differentiation of SH-SY5Y Neuroblastoma Cells," *Journal of Biological Chemistry,* Oct. 22, 1999;274(43): 30341–30344.

Kandel et al., "Principles of Neural Science," 4$^{th}$ Ed.; 2002: 67–81, 85–86.

Kim et al., "Insulin-like Growth Factor-I-mediated Neurite Outgrowth in Vitro Requires Mitogen-activated Protein Kinase Activation," *Journal of Biological Chemistry,* Aug. 22, 1997;272(34): 21268–21273.

Kim et al., "Differential Regulation of Insulin Receptor Substrate-2 and Mitogen-Activated Protein Kinase Tyrosine Phosphorylation by Phosphatidylinositol 3-Kinase Inhibitors in SH-SY5Y Human Neuroblastoma Cells," *Endocrinology,* 1998;139(12): 4881–4889.

Lachyankar et al., "A Role for Nuclear PTEN in Neuronal Differentiation," *Journal of Neuroscience,* Feb. 15, 2000;20(4): 1404–1413.

Ley et al., "Adhesion Molecules in Lymphocyte Trafficking and Colitis," *Gastroenterology,* Oct. 2001;121(4):Editorial: 1008–1010.

Noble et al., "Overexpression of Dynamin is Induced by Chronic Stimulation of μ– but Not δ–Opioid Receptors: Relationships with μ–Related Morphine Dependence," *Molecular Pharmacology,* 2000;58: 159–166.

Ponthan et al., "The Synthetic Retinoid RO 13–6307 induces Neuroblastoma Differentiation in vitro and inhibits Neuroblastoma Tumour growth in vivo," *Int. J. Cancer,* 2003;104: 418–424.

Popik et al., "Cognitive effects of Colostral-Val nonapeptide in aged rats," *Behavioral Brain Research,* Jan. 29, 2001;118(2): 201–208.

Puglianiello et al., "IGF–I stimulates chemotaxis of human neuroblasts. Involvement of type 1 IGF receptor, IGF binding proteins, phosphatidylinositol–3 kinase pathway and plasmin system," *Journal of Endocrinology,* 2000;165: 123–131.

Salmi et al., "Immune Cell Trafficking in Uterus and Early Life is Dominated by the Mucosal Addressin MadCAM–1 in Humans," *Gastroenterology,* Oct. 2001;121(4): 853–864.

Xiang–Ming et al., "Gating kinetics of potassium channel and effects of nerve growth factors in PC12 cells analyzed with fractal model," *Acta Pharmacol Sin,* Feb. 2001;22(2): 103–110.

Zhen et al., "Lithium regulates protein tyrosine phosphatase activity in vitro and in vivo," *Psychopharmacology,* 2002;162: 379–384.

Cosgaya et al., "Neuronal differentiation of PC12 cells induced by engrailed homeodomain is DNA–binding specific and independent of MAP kinases," *Journal of Cell Science,* 1998;111:2377–2384.

Vaudry et al., "Signaling Pathways for PC12 Cell Differentiation: Making the Right Connections," *Science* May 31, 2002;296: 1648–1649.

Kimball, John W., "White Blood Cells (leukocytes)," *Kimball's Biology Papers* [online], [retrieved on Dec. 2, 2002]. Retrieved from the internet: <http://users.rcn.com/jkimball.ma.ultranet/BiologyPages/B/Blood.html.; 2 pgs.

Leszek et al., "Colostrinin® proline–rich polypeptide complex from ovine colostrum—a long–term study of its efficacy in Alzheimer's Disease," (2002) *Med Sci Monit;* 8(10):PI93–96.

Rao, "Multipotent and Restricted Precursors in the Central Nervous System," (1999) *The Anatomical Record (New Anat.)*;257:137–148.

Schwab, "Repairing the Injured Spinal Cord," (2002) *Science;* 295:1029–1031.

Boldogh et al., "Modulation of 4HNE–Mediated Signaling by proline–rich peptides form Ovine Colostrum," *J Mol Neuroscience,* May 2003;20(2): 125–134.

Brown et al., "7–Hydroperoxycholesterol and its products in oxidized low density lipoprotein and human atherosclerotic plaque," *J. Lipid Res,* 1997; 38: 1730–1745.

Bruce-Keller et al., "4–Hydroxynonenal, a product of lipid peroxidation, damages cholinergic neurons and impairs visuospatial memory in rats," *J Neuropathol Exp Neurol,* 1998;57: 257–267.

Buettner, G.R., "The pecking order of free radicals and antioxidants: lipid peroxidation, alpha-tocopherol, and ascorbate," *Arch Biochem Biophys,* 1993;300: 535–543.

Cadenas et al., "Mitochondrial free radical generation, oxidative stress, and aging," *Free Radic Biol Med,* 2000;29:222–230.

Camandola et al., "The lipid peroxidation product 4–hydroxy–2,3–nonenal inhibits constitutive and inducible activity of nuclear factor kappa B in neurons," *Brain Res Mol Brain Res,* 2000;85:53–60.

Cheng et al., "Effects on mGST A4 transfection on 4–hydroxynonenal–mediated apoptosis and differentiation of K562 human erythroleukemia cells," *Arch Biochem Biophys,* 1999;372: 29–36.

Davies et al., "Photo–oxidation of proteins and its role in cataractogenesis," *J. Photochem. Photobiol B,* 2001;63: 114–125.

Davis et al., "Cellular thiols and rective oxygen species in drug–induced apoptosis," *J. Pharmacol Exp. Ther,* 2001;296: 1–6.

DeZwart et al., "Biomarkers of free radical damage applications in experimental animals and in humans," *Free Radic Biol Med,* 1999; 26:202–226.

Evan et al., "A matter of life and cell death," *Science,* 1998;281: 1317–1322.

Finkel et al., "Oxidants, oxidative stress and the biology of ageing," *Science,* 1998;281: 1317–1322.

Friguet et al., "Protein degradation by the proteasome and its implications in aging," *Ann N Y Acad Sci,* 2000;908: 143–154.

Gage et al., "Isolation, Characterization, and use of Stem Cells from the CNS," *Annu. Rev. Neurosci,* 1995; 18: 159–92.

Gardner et al., "Development of a peptide antibody specific to human glutathione S–transferase alpha 4–4 (hGSTA4–4) reveals preferential localization in human liver mitochondria," *Arch Biochem Biophys,* 2001;390: 19–27.

Hainut et al., "Redox modulation of p53 conformation and sequence–specific DNA binding in vitro," *Cancer Res,* 1993;53: 4469–4473.

Han et al., "Implication of a small GTPase Rac1 in the activation of c–Jun–N–terminal kinase and heat shock factor in response to heat shock," *J Biol Chem,* 2001; 276:1889–1895.

Hughes et al., "Mediation of nerve growth factor–driven cell cycle arrest in PC12 cells by p53. Simultaneous differentiation and proliferation subsequent to p53 functional inactivation," *J Biol Chem,* 2000;275: 37829–37837.

Janusz et al., "Immunoregulatory properties of synthetic peptides, fragments of a proline–rich polypeptide (PRP) from ovine colostrum," *Molecular Immunology,* Oct. 1987;24(10): 1029–1031.

Keller et al., "Mitochondrial manganese superoxide dismutase prevents neural apoptosis and reduces ischemic brain injury: suppression of peroxynitrite production, lipid peroxidation, and mitochondrial dysfuention," *J Neurosci,* 1998; 18: 687–697.

Kong et al., "Signal transduction events elicited by natural products: a role of MAPK and caspase pathways in homeostatic response and induction of apoptosis," *Arch Pharm Res,* 2000;23: 1–16.

Kruman et al., "Evidence that 4–hydroxynonenal mediates oxidative stress–induced neuronal apoptosis," *J Neurosci,* 1997;17:5089–5100.

Lafon-Cazal et al., "Nitric oxide, superoxide and peroxynitrite: putative mediators of NMDA–induced cell death in cerebellar granule cells," *Neuropharmacology,* 1993;32: 1259–1266.

Leonarduzzi et al., "Lipid oxidation products in cell signaling," *Free Radic Biol Med,* 2000;28: 1370–1378.

Mattson et al., "Alzheimer's disease. Short Precursor shortens memory," *Nature,* 1997;387: 457–458.

Nakamura et al., "Redox regulation of cellular activation," *Annu Rev Immunol,* 1997;15: 351–369.

Page et al., "4–Hydroxynonenal prevents NF–kappaB activation and tumor necrosis factor expression by inhibiting IkappaB phosphorylation and subsequent proteolysis," *J Biol Chem,* 1999;274:11611–11618.

Parola et al., "HNE interacts directly with JNK isoforms in human hepatic stellate cells," *J Clin Invest,* 1998;102:1942–1950.

Perkins et al., "Association of antioxidants with memory in a multiethnic elderly sample using the Third National Health and Nutrition Examination Survey," *Am J Epidemiol,* 1999;150: 37–44.

Perrig et al., "The relation between antioxidants and memory performance in the old and very old," *J Am Geriatr Soc,* 1997;45: 718–724.

Poli et al., "4–Hydroxynonenal in the pathomechanisms of oxidative stress," *IUBMB Life,* 2000;50: 315–321.

Rivas-Arancibia et al., "Effects of ozone exposure in rats on memory and levels of brain and pulmonary superoxide dismutase," *Environ Res,* 1998;76: 33–39.

Ross et al., "Atherosclerosis: a cancer of the blood vessels?," *Am J Clin Pathol 116 Suppl,* 2001:S97–107.

Rusnak et al., "Sensing electrons: protein phosphatase redox regulation," *Trends Biochem Sci,* 2000;25: 527–529.

Sano et al., "A controlled trial of selegiline, alpha–tocopherol, or both as treatment for Alzheimer's disease," *The Alzheimer's Disease Cooperative Study, N Engl J Med,* 1997;336:1216–1222.

Sayre et al., "4–Hydroxynonenal–derived advanced lipid peroxidation end products are increased in Alzheimer's disease," *J Neurochem,* 1997;68: 2092–2097.

Senft et al., "Determining glutathione and glutathione disulfide using the fluorescense probe o–phthaladehyde," *Anal Biochem,* 2000; 280: 80–86.

Sinclair et al., "Altered plasma antioxidant status in subjects with Alzheimer's disease and vascular dementia," *Int J Geriatr Psychiatry,* 1998;13: 840–845.

Uchida et al., "Modification of histidine residues in proteins by reaction with 4-hydroxynonenal," *Proc Natl Acad Sci USA*, 1992;89:4544–4548.

Vaglini et al., "Cytochrome P450 and parkinsonism: protective role of CYP2E1," *Funct Neurol*, 2001;16: 107–112.

Woods et al., "Regulation of p53 function," *Exp Cell Res*, 2001;264: 56–66.

Yoritaka et al., "Immunohistochemical detection of 4-hydroxynonenal protein adducts in Parkinson disease," *Proc Natl Acad Sci USA*, 1996;93: 2696–2701.

Zimecki et al., "Immunotropic properties of fractions isolated from human milk," *Arch Immunol Ther Exp*, 1984;32:203–209.

Zimecki et al., "The effect of a proline-rich polypeptide (PRP) on the humoral immune response. II. PRP induces differentiation of helper cells from glass-nonadherent thymocytes (NAT) and suppressor cells from glass-adherent thymocytes (GAT)," *Arch Immunol Ther Exp*, 1984;32: 197–201.

Zimecki et al., "The effect of a poline-rich polypeptide (PRP) on the humoral immune response. I. Distinct effect of PRP on the T cell properties of mouse glass-nonadherent (NAT) and glass-adherent (GAT) thymocytes in thymectomized mice," *Arch Immunol Ther Exp*, 1984;32: 191–196.

\* cited by examiner

USE OF COLOSTRININ, CONSTITUENT PEPTIDES THEREOF, AND ANALOGS THEREOF FOR INDUCING CYTOKINES

CROSS-REFERENCE TO RELATED APPLICATIONS

The present application claims priority from U.S. patent application No. 60/149,311, filed on Aug. 17, 1999, which is incorporated herein by reference.

BACKGROUND OF THE INVENTION

Colostrum is a component of the milk of mammals during the first few days after birth. Colostrum is a thick yellowish fluid and is the first lacteal secretion post parturition and contains a high concentration of immunoglobins (IgG, IgM, and IgA) and a variety of non-specific proteins. Colostrum also contains various cells such as granular and stromal cells, neutrophils, monocyte/macrophages, and lymphocytes. Colostrum also includes growth factors, hormones, and cytokines. Unlike mature breast milk, colostrum contains low sugar, low iron, but is rich in lipids, proteins, mineral salts, vitamins, and immunoglobins.

Colostrum also includes or contains a proline-rich polypeptide aggregate, which is referred to as colostrinin. One peptide fragment of colostrinin is Val-Glu-Ser-Tyr-Val-Pro-Leu-Phe-Pro (SEQ ID NO:31), which is disclosed in International Publication No. WO-A-98/14473. Colostrinin and this fragment have been identified as useful in the treatment of disorders of the central nervous system, neurological disorders, mental disorders, dementia, neurodegenerative diseases, Alzheimer's disease, motor neurone disease, psychosis, neurosis, chronic disorders of the immune system, diseases with a bacterial and viral aetiology, and acquired immunological deficiencies as set forth in International Publication No. WO-A-98/14473.

Although certain uses for colostrinin have been identified, it would represent an advancement in the art to discover and disclose other uses for colostrinin, or a component thereof, that are not readily ascertainable from the information currently known about colostrinin or its constituents.

SUMMARY OF THE INVENTION

The present invention relates to the use of colostrinin, at least one constituent (i.e., component) peptide thereof, at least one active analog thereof (e.g., peptide having an N-terminal sequence equivalent to an N-terminal sequence of at least one of the colostrinin constituent peptides), and combinations thereof, as a cytokine-inducing agent. These agents can be used as immunological regulators to modulate (e.g. enhance, inhibit, modify, augment, or otherwise alter, and preferably promote) specific or nonspecific immune responses in patients, particularly animals including mammals such as humans. They can also be used as blood cell regulators to modulate (e.g., enhance, inhibit, modify, augment, or otherwise alter, preferably, and promote) cellular proliferation or differentiation (preferably, promoting proliferation and differentiation) of blood cells, such as leukocytes.

In one embodiment, the present invention provides a method of inducing a cytokine in a cell. The method includes contacting the cell with an immunological regulator under conditions effective to induce (i.e., induce the synthesis or production of) at least one cytokine (either directly or indirectly), wherein the immunological regulator is selected from the group of MQPPPLP (SEQ ID NO:1); LQTPQ-PLLQVMMEPQGD (SEQ ID NO:2), DQPPDVEKP-DLQPFQVQS (SEQ ID NO:3); LFFFLPVVNVLP (SEQ ID NO:4); DLEMPVLPVEPFPFV (SEQ ID NO:5); MPQN-FYKLPQM (SEQ ID NO:6); VLEMKFPPPPQETVT (SEQ ID NO:7); LKPFPKLKVEVFPFP (SEQ ID NO:8); VVMEV (SEQ ID NO:9); SEQP (SEQ ID NO:10); DKE (SEQ ID NO:11); FPPPK (SEQ ID NO:12), DSQPPV (SEQ ID NO:13), DPPPPQS (SEQ ID NO:14), SEEMP (SEQ ID NO:15); KYKLQPE (SEQ ID NO:16); VLPPNVG (SEQ ID NO:17); VYPFTGPIPN (SEQ ID NO:18); SLPQNILPL (SEQ ID NO:19); TQTPVVVPPF (SEQ ID NO:20); LQPE-IMGVPKVKETMVPK (SEQ ID NO:21); HKEMPFP-KYPVEPFTESQ (SEQ ID NO:22); SLTLTDVEKLHL-PLPLVQ (SEQ ID NO:23); SWMHQPP (SEQ ID NO:24); QPLPPTVMFP (SEQ ID NO:25); PQSVLS (SEQ ID NO:26); LSQPKVLPVPQKAVPQRDMPIQ (SEQ ID NO:27); AFLLYQE (SEQ ID NO:28); RGPFPILV (SEQ ID NO:29); ATFNRYQDDHGEEILKSL (SEQ ID NO:30); FLLYQEPVLGPVR (SEQ ID NO:32); LNF (SEQ ID NO:33); and MHQPPQPLPPTVMFP (SEQ ID NO:34); an active analog thereof; and combinations thereof; with the proviso that the immunological regulator is not VESYV-PLFP (SEQ ID NO:31). The cell can be in a cell culture, a tissue, an organ or an organism. Hence, this method can be carried out *in vivo* or *in vitro*.

In another embodiment, there is provided a method for modulating an immune response in a cell. The method includes contacting the cell with an immunological regulator under conditions effective to induce at least one cytokine, wherein the immunological regulator is listed above. The cell can be in a cell culture, a tissue, an organ, or an organism. Hence, this method can be carried out *in vivo* or *in vitro*.

In yet another embodiment, there is provided a method for modulating an immune response in a patient. The method includes administering to the patient an immunological regulator under conditions effective to induce at least one cytokine, wherein the immunological regulator is listed above.

The immune response can be specific or nonspecific. Typically, one or more cytokines are directly induced using the polypeptides described herein, which then results in an upregulation or a downregulation of one or more other cytokines. Thus, using various combinations of polypeptides described herein, various cytokine profiles and immune responses can be produced, which may be specific or nonspecific. Examples of such immune responses include the interferon response and antibody production. As long as at least one cytokine level increases, whether it be increased as a result of direct inducement by one of the peptides described herein, or as a result of indirect inducement (e.g., through the interaction with another cytokine), a peptide is "active" as used herein.

In another embodiment, there is provided a method for modulating blood cell proliferation. The method includes contacting blood cells with a blood cell regulator selected from the group of colostrinin, a constituent peptide thereof, an analog thereof, and combinations thereof, under conditions effective to change the number of blood cells. The blood cells can be in a cell culture or an organism. Hence, this method can be carried out *in vivo* and *in vitro*.

In still another embodiment, there is provided a method for modulating blood cell proliferation in a patient (preferably, a human patient). The method includes administering to the patient a blood cell regulator selected from the group of colostrinin, a constituent peptide thereof, an analog thereof, and combinations thereof, under conditions effective to change the number of blood cells.

The blood cells can be mammalian blood cells, such as human blood cells. Preferably, the blood cells are increased in number, athough a decrease in number can also be desirable in certain situations such as leukemia, myeolopathy etc. More preferably, the blood cells are increased in number and differentiated. The blood cell regulator is preferably a constituent peptide of colostrinin.

In other embodiments, the invention provides the use of an immunological regulator or blood cell regulator in the manufacture of a medicament for use in the methods described herein.

The present invention also provides an immune-inducing composition that includes a pharmaceutical carrier and an active agent selected from the MQPPPLP (SEQ ID NO:1); LQTPQPLLQVMMEPQGD (SEQ ID NO:2); DQPPDVEKPDLQPFQVQS (SEQ ID NO:3); LFFFLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPFPKLKVEVFPFP (SEQ ID NO:8); VVMEV (SEQ ID NO:9); SEQP (SEQ ID NO:10); DKE (SEQ ID NO:11); FPPPK (SEQ ID NO:12); DSQPPV (SEQ ID NO:13); DPPPPQS (SEQ ID NO:14); SEEMP (SEQ ID NO:15); KYKLQPE (SEQ ID NO:16); VLPPNVG (SEQ ID NO:17); VYPFTGPIPN (SEQ ID NO:18); SLPQNILPL (SEQ ID NO:19); TQTPVVVPPF (SEQ ID NO:20); LQPEIMGVPKVKETMVPK (SEQ ID NO:21); HKEMPFPKYPVEPFTESQ (SEQ ID NO:22); SLTLTDVEKLHLPLPLVQ (SEQ ID NO:23); SWMHQPP (SEQ ID NO:24); QPLPPTVMFP (SEQ ID NO:25); PQSVLS (SEQ ID NO:26); LSQPKVLPVPQKAVPQRDMPIQ (SEQ ID NO:27); APLLYQE (SEQ ID NO:28); RGPFPILV (SEQ ID NO:29); ATFNRYQDDHGEEILKSL (SEQ ID NO:30); FLLYQEPVLGPVR (SEQ ID NO:32); LNF (SEQ ID NO:33); and MHQPPQPLPPTVMFP (SEQ ID NO:34); an active analog thereof; and combinations thereof; with the proviso that the immunological regulator is not VESYVPLFP (SEQ ID NO: 31).

As used herein, "a" or "an" means one or more (or at least one), such that combinations of active agents (i.e., active immunological regulators or blood cell differentiation promoters), for example, can be used in the compositions and methods of the invention. Thus, a composition that includes "a" polypeptide refers to a composition that includes one or more polypeptides.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

DETAILED DESCRIPTION OF PREFERRED EMBODIMENTS OF THE INVENTION

The inventors have found that colostrinin, at least one constituent (i.e., component) peptide thereof, and/or at least one active analog thereof (e.g., a peptide having an N-terminal sequence equivalent to an N-terminal sequence of at least one of the colostrinin constituent peptides) can be used to induce at least one cytokine (e.g., TNF-α, IFN-γ, IL-1, IL-2, IL-4, IL-6, I-10, IL-12). The cytokine can be either directly or indirectly induced. This can result in the modulation of an immune response or blood cell proliferation or differentiation (preferably, the promotion of blood cell proliferation, and more preferably, the promotion of blood cell proliferation and differentiation) *in vitro* and *in vivo*, in animals (including mammals such as humans).

Such immunological regulators and blood cell regulators are referred to herein as "active agents." Significantly, such agents can be administered alone or in various combinations to a patient (e.g., animals including humans) as a medication or dietary (e.g., nutrient) supplement in a dose sufficient to modulate one or more immune responses throughout the patient's body, in a specific tissue site, or in a collection of tissue sites.

Many nonspecific and specific immune responses are associated with leukocyte proliferation and differentiation. The overall immunological significance of the present invention can be, but it not limited to, the following: IFN-γ is a potent immunomodulater that is important for the development of the cytotoxic lymphocyte response (CTL). This immune response is considered to be very important in protecting humans and animals from a variety of bacterial, viral, parasitic, and fungal diseases. The fact that TNF-α is also induced is important because TNF-α is a major activator of macrophages, among other immune cells, which are important in host defense against infections. In addition, TNF-α has been shown to have activity against cancer, directly through its lytic activity and indirectly through macrophages. IL-10 is another important immune mediator that controls both IFN-γ and TNF-α production and action. Its production represent a negative feedback control for IFN-γ and TNF-α production. Another one of its hallmark activities is the control of antibody production during the humoral immune responses, which is certainly important in many types of infections. In addition to IL-10's immune activities, it also has been shown to play a role in the neuroendocrine system by modulating certain stress responses and immune responses. IL-10 has been shown to induce the production of corticotropin from pituitary cells. Corticotropin works downstream in the hypothalmic adrenal axis to induce glucocortico steroids that are inherently immunomodulatory. Like IL-10, the IL-4 is important in the development of B cell responses, which are the mediators of the humoral immune response. Finally, the IL-12 is an important IFN-γ inducer. Taken together these findings suggest that colostrinin and its component peptides have the ability to modulate via cytokine induction a variety of host-defense mechanisms mediated by macrophages and lymphocytes at the cellular and humoral immune level as well as the neuroendocrine system.

Thus, the methods and compositions of the present invention can be utilized to control immunological and blood cell differentiating activity. The active agents described herein can be used individually, in various combinations, or combined with other previously known or newly invented pharmacological agents, such as antioxidants. They can be used as adjuvants for existing vaccinations as well.

In a preferred embodiment, the present invention provides a method for modulating an immune response. Whether it be *in vivo* or *in vitro*, this method involves monitoring the level of at least one cytokine, which can be done by known methods, such as disclosed by Inglot et al., *Arch. Immunol. Ther. Exp.*, 44, 215-224 (1996); Blach-Olszewska et al., *Arch. Immunol. Ther. Exp.*, 45, 43-47 (1997); Piasecki et al., *Arch. Immunol. Ther. Exp.*, 45, 109-117 (1997); Hughes et al., *Int. J. Immunopharmacol.*, 17, 857-863 (1995); and Mishell et al., *Selected Methods in Cellular Immunology*, W.H. Freeman, 1980. Specific *in vitro* methods are described in the Examples Section.

In another preferred embodiment, the present invention provides a method for modulating blood cell proliferation (preferably, proliferation and differentiation). Whether it be *in vivo* or *in vitro*, this method involves monitoring the level of increase or decrease in the number of blood cells bearing a specific phenotypic marker (for differentiation, the types of cells formed are evaluated), as disclosed by Kim et al., *Clin. Lab. Haematol.*, 20, 21-29 (1998); Grunwald et al., *Methods Mol. Biol.*, 119, 443-454 (1999); Villas et al., *Cell. Vis.*, 5, 56-61 (1998); and Gratama et al., *Cytometry*, 33, 166-178 (1998). Specific *in vitro* methods are described in the Examples Section.

The peptides described herein may be used for the proliferation and/or differentiation of other types of cells as well.

Colostrinin is composed of peptides, the aggregate of which has a molecular weight range between about 5.8 to about 26 kiloDaltons (kDa) determined by polyacrylamide gel electrophoresis. It has a greater concentration of proline than any other amino acid. Ovine colostrinin has been found to have a molecular weight of about 18 kDa and includes three non-covalently linked subunits having a molecular weight of about 6 kDa and has about 22 wt-% proline. Ovine colostrinin has also been shown to contain the following number of residues per subunit: lysine-2; histidine-1; arginine-0; aspartic acid-2; threonine-4; serine-3; glutamic acid-6; proline-11; glycine-2; alanine-0; valine-5; methionine-2; isoleucine-2; leucine-6; tyrosine-1; phenylalanine-3; and cysteine-0.

Colostrinin has been found to include a number of peptides ranging from 3 amino acids to 22 amino acids or more. These can be obtained by various known techniques, including isolation and purification involving eletrophoresis and synthetic techniques. The specific method of obtaining colostrinin and SEQ ID NO:31 is described in International Publication No. WO-A-98/14473. Using HPLC and Edelman Degradation, over 30 constituent peptides of colostrinin have been identified, which can be classified into several groups: (A) those of unknown precursor; (B) those having a β-casein homologue precursor; (C) those having a β-casein precursor; and (D) those having an annexin precursor. These peptides are described in International Patent Publication No. WO 00/75173, filed Jun. 2, 2000, claiming priority to Jun. 2, 1999, and can be synthesized according to the general method described in the Examples Section. These peptides (i.e., constituent peptides of colostrinin), which can be derived from colostrinin or chemically synthesized, include: MQPPPLP (SEQ ID NO:1); LQTPQPLLQVMMEPQGD (SEQ ID NO:2); DQPPDVEKPDLQPFQVQS (SEQ ID NO:3); LFFFLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPFPKLKVEVFPFP (SEQ ID NO:8); VVMEV (SEQ ID NO:9); SEQP (SEQ ID NO:10); DKE (SEQ ID NO:11); FPPPK (SEQ ID NO:12); DSQPPV (SEQ ID NO:13); DPPPPQS (SEQ ID NO:14); SEEMP (SEQ ID NO:15); KYKLQPE (SEQ ID NO:16); VLPPNVG (SEQ ID NO:17); VYPFTGPIPN (SEQ ID NO:18); SLPQNILPL (SEQ ID NO:19); TQTPVVVPPF (SEQ ID NO:20); LQPEIMGVPKVKETMVPK (SEQ ID NO:21); HKEMPFPKYPVEPFTESQ (SEQ ID NO:22); SLTLTDVEKLHLPLPLVQ (SEQ ID NO:23); SWMHQPP (SEQ ID NO:24); QPLPPTVMFP (SEQ ID NO:25); PQSVLS (SEQ ID NO:26); LSQPKVLPVPQKAVPQRDMPIQ (SEQ ID NO:27); AFLLYQE (SEQ ID NO:28); RGPFPILV (SEQ ID NO:29); ATFNRYQDDHGEEILKSL (SEQ ID NO:30); VESYVPLFP (SEQ ID NO:31); FLLYQEPVLGPVR (SEQ ID NO:32); LNF (SEQ ID NO:33); and MHQPPQPLPPTVMFP (SEQ ID NO:34). These can be classified as follows: (A) those of unknown precursor include SEQ ID NOs:2, 6, 7, 8, 10, 11, 14, and 33; (B) those having a β-casein homologue precursor include SEQ ID NOs:1, 3, 4, 5, 9, 12, 13, 15, 16, 17, and 31; (C) those having a β-casein precursor include SEQ ID NOs:18 (casein amino acids 74–83), 19 (casein amino acids 84–92), 20 (casein amino acids 93–102), 21 (casein amino acids 103–120), 22 (casein amino acids 121–138), 23 (casein amino acids 139–156), 24 (casein amino acids 157–163), 25 (casein amino acids 164–173), 26 (casein amino acids 174–179), 27 (casein amino acids 180–201), 28 (casein amino acids 202–208), 29 (casein amino acids 214–222), 32 (casein amino acids 203–214), and 34 (casein amino acids 159–173); and (D) those having an annexin precursor include SEQ ID NO:30 (annexin amino acids 203–220).

For certain embodiments, a preferred group of such peptides does not include SEQ ID NO:31. A more preferred group of such peptides includes: MQPPPLP (SEQ ID NO:1); LQTPQPLLQVMMEPQGD (SEQ ID NO:2); DQPPDVEKPDLQPFQVQS (SEQ ID NO:3); LFFFLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPFPKLKVEVFPFP (SEQ ID NO:8); VYPFTGPIPN (SEQ ID NO:18), SLPQNILPL (SEQ ID NO:19), TQTPVVVPPF (SEQ ID NO:20), HKEMPFPKYPVEPFTESQ (SEQ ID NO:22), and combinations thereof.

The polypeptides of SEQ ID NOs:1–34 can be in their free acid form or they can be amidated at the C-terminal carboxylate group. The present invention also includes analogs of the polypeptides of SEQ ID NOs:1–34, which includes polypeptides having structural similarity with SEQ ID NOs:1–34. These peptides can also form a part of a larger peptide. An "analog" of a polypeptide includes at least a portion of the polypeptide, wherein the portion contains deletions or additions of one or more contiguous or noncontiguous amino acids, or containing one or more amino acid substitutions. An "analog" can thus include additional amino acids at one or both of the terminii of the polypeptides listed above. Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains); Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Preferably, active analogs of colostrinin and its constituent peptides include polypeptides having a relatively large number of proline residues. Because proline is not a common amino acid, a "large number" preferably means that a polypeptide includes at least about 15% proline (by number), and more preferably at least about 20% proline (by number). Most preferably, active analogs include more proline residues than any other amino acid. For certain embodiments, preferred group of such active analogs does not include SEQ ID NO:31.

As stated above, active analogs of colostrinin and its constituent peptides include polypeptides having structural similarity. Structural similarity is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, available on the worldwide web at ncbi.nlm.nih.gov/gorf/b12.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, an active analog of colostrinin or its constituent peptides has a structural similarity to colostrinin or one or more of its constituent peptides (preferably, one of SEQ ID NOs:1–34) of at least about 70% identity, more preferably, at least about 80% identity, and most preferably, at least about 90% identity.

Colostrinin or any combination of its peptide components or active analogs thereof can be derived (preferably, isolated and purified) naturally such as by extraction from colostrum or can be synthetically constructed using known peptide polymerization techniques. For example, the peptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in *Synthetic Peptides: A User's Guide*, W. M. Freeman & Company, New York, N.Y., pp. 77–183 (1992). Moreover, gene sequence encoding the colostrinin peptides or analogs thereof can be constructed by known techniques such as expression vectors or plasmids and transfected into suitable microorganisms that will express the DNA sequences thus preparing the peptide for later extraction from the medium in which the microorganism are grown. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The peptides used in the methods of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary, but from about 4 to 8 peptides per carrier molecule are typically obtained under standard coupling conditions.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. For example, conjugates of a peptide coupled to ovalbumin may be prepared by dissolving equal amounts of lyophilized peptide and ovalbumin in a small volume of water. In a second tube, 1-ethyl-3-(3-dimethylaminopropyl)-carbodiimide hydrochloride (EDC; ten times the amount of peptide) is dissolved in a small amount of water. The EDC solution was added to the peptide/ovalbumin mixture and allowed to react for a number of hours. The mixture may then dialyzed (e.g., into phosphate buffered saline) to obtain a purified solution of peptide/ovalbumin conjugate.

Peptide/carrier molecule conjugates prepared by this method typically contain about 4 to 5 peptides per ovalbumin molecule.

The present invention also provides a composition that includes one or more active agents (i.e., colostrinin, at least one constituent peptide thereof, or active analog thereof) of the invention and one or more carriers, preferably a pharmaceutically acceptable carrier. The methods of the invention include administering to, or applying to the skin of, a patient, preferably a mammal, and more preferably a human, a composition of the invention in an amount effective to produce the desired effect. The active agents of the present invention are formulated for enteral administration (oral, rectal, etc.) or parenteral administration (injection, internal pump, etc.). The administration can be via direct injection into tissue, interarterial injection, intervenous injection, or other internal administration procedures, such as through the use of an implanted pump, or via contacting the composition with a mucus membrane in a carrier designed to facilitate transmission of the composition across the mucus membrane such as a suppository, eye drops, inhaler, or other similar administration method or via oral administration in the form of a syrup, a liquid, a pill, capsule, gel coated tablet, or other similar oral administration method. The active agents can be incorporated into an adhesive plaster, a patch, a gum, and the like, or it can be encapsulated or incorporated into a bio-erodible matrix for controlled release.

The carriers for internal administration can be any carriers commonly used to facilitate the internal administration of compositions such as plasma, sterile saline solution, IV solutions or the like. Carriers for administration through mucus membranes can be any well-known in the art. Carriers for administration oral can be any carrier well-known in the art.

The formulations may be conveniently presented in unit dosage form and may be prepared by any of the methods well known in the art of pharmacy. All methods include the step of bringing the active agent into association with a carrier which constitutes one or more accessory ingredients. In general, the formulations are prepared by uniformly and intimately bringing the active agent into association with a liquid carrier, a finely divided solid carrier, or both, and then, if necessary, shaping the product into the desired formulations.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. The amount of active agent is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, DMSO, polyhydroxy alcohols, or other bases used for topical pharmaceutical formulations.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

EXAMPLES

The invention will be further described by reference to the following detailed examples. The examples are meant to provide illustration and should not be construed as limiting the scope of the present invention. All peptides were dissolved in a balanced salt solution and/or DMSO.

Preparation of Peptides:

1. Wash pre-loaded resin with DMF (dimethylformamide), then drain completely.

2. Add 10 ml of 20% piperidine/DMF to resin. Shake for 5 minutes, then drain.

3. Add another 10 ml of 20% piperidine/DMF. Shake for 30 minutes.

4. Drain reaction vessel and wash resin with DMF four times. Then wash once with DCM (dichloromethanol). Check beads using the ninhydrin test - the beads should be blue.
5. The coupling step was carried out as follows:
   a. Prepare the following solution: 1 mmole Fmoc (i.e. fluorenylmethyloxycarbonyl) amino acid 2.1 ml of 0.45 M HBTU/HOBT (1 mmol) (2-(1H-benzotriazol-1-yl)-1,1,3,3-tetramethyluronium hexafluorophosphate/N-hydroxybenzotraizole-$H_2O$) 348 µl of DIEA (2 mmol) (diisopropylethylamine); and
   b. Add the solution to the resin and shake for a minimum of 30 minutes.
6. Drain reaction vessel and wash the resin again with DMF four times and with DCM once.
7. Perform the ninhydrin test: If positive (no colour) - proceed to step 2 and continue synthesis; If negative (blue colour) - return to step 5 and recouple the same Fmoc amino acid.
8. After the synthesis was complete, the peptide was cleaved from the resin with 5% $H_2O$, 5% phenol, 3% Thionisole, 3% EDT (ethanedithiol), 3% triisopropylsilane and 81% TFA for 2 hours.
9. After 2 hours, filter into cold MTBE (methyl t-butyl ether). The precipitated peptide was then washed twice with cold MTBE and dried under nitrogen gas.
10. The molecular weight of the synthesised was checked by Matrix-Assisted Laser Desorption Time-of-Flight Mass Spectroscopy (LDMS), and the purity was checked by HPLC using a C-18, 300 Angstrom, 5 µm column.

Induction of Blood Cell Proliferation:

The quantity of peripheral blood leukocyte (PBL) stimulation was determined by measuring the amount of $^3$H-thymidine (1.0 to 2.0 µC thymidine/culture) incorporated into triplicate cultures (4×10$^5$ PBLs/culture) stimulated with colostrinin and its constituent peptides (CCP) for 72 hours. $^3$H-thymidine was then added and allowed to incorporate for 24 hours. Staphylococcal enterotoxin A (SEA, also referred to as "super antigen"), a specific T cell mitogen, was used as a positive control and for comparative purposes. Colostrum and low and high iron containing baby formulas diluted 1:5 and 1:10 were also used in some experiments to determine the relative stimulatory activity of these products. Radioactivity was measured in a Matrix 9600 Direct Beta Counter. Six replicas of medium treated cultures were used to determine the mean background incorporated counts. The data is expressed as the mean $^3$H-thymidine counts per minute (CPM) above background. Results of one out of a total of six experiments is shown below in Table 1.

It can be seen that colostrinin and its constituent peptides are excellent inducers of PBL proliferation. Active concentrations ranged from 100 µg/ml to 0.1 µg/ml. Nine peptides and colostrinin and colostrum were tested. Certain peptides appeared to have greater activity than others with the maximum increase in proliferative activity being roughly 10 times above background. It appears that with many of the peptides, the active range of proliferation induction was present since concentrations as low as 0.1 µg/ml still had potent activity. Some of the peptides had more activity than colostrinin alone. Another interesting finding is that colostrum appears to have roughly an equivalent amount of activity as colostrinin. SEA has the greatest activity and this is also not unexpected due to its classification as a super antigen. PBL proliferation is an important part of the immune response both for generating antigen reactive cells and induction of numerous modulating cytokines. In the newborn these processes are essential as a building block for development of an optimal immune response and provide a protective host defense barrier against diseases associated with the neonatal gut.

TABLE 1

Effect of CCP on Fresh Human Leukocyte Cultures

| Peptide | Peptide Conc. µg/ml | Slide No. | Microscope 3 plus to 0 | Mitogenic Activity CPM |
|---|---|---|---|---|
| SEQ ID NO:1 | 100 | 1 | +++ | 1259 |
|  | 10 | 2 | ++ | 4856 |
|  | 1.0 | 3 | + | 4829 |
|  | 0.1 | 4 | +/− | 3339 |
| SEQ ID NO:7 | 100 | 5 | ++ | 1383 |
|  | 10 | 6 | + | 3478 |
|  | 1.0 | 7 | +/− | 2290 |
|  | 0.1 | 8 | − | 584 |
| SEQ ID NO:8 | 100 | − | − | 2039 |
|  | 10 | 9 | − | 1810 |
|  | 1.0 | 10 | +++ | 1527 |
|  | 0.1 | 11 | ++ | 2177 |
| SEQ ID NO:3 | 100 | ND | − | 469 |
|  | 10 | ND | − | 819 |
|  | 1.0 | ND | − | 3323 |
|  | 0.1 | ND | − | 86 |
| SEQ ID NO:2 | 100 | ND | − | 29 |
|  | 10 | 12 | − | 2989 |
|  | 1.0 | 13 | ++ | 4809 |
|  | 0.1 | 14 | +/− | 3578 |
| SEQ ID NO:4 | 100 | 15 | + | 2667 |
|  | 10 | 16 | + | 4915 |
|  | 1.0 | ND | − | 4050 |
|  | 0.1 | ND | − | 3523 |
| SEQ ID NO:5 | 100 | ND | − | 1762 |
|  | 10 | ND | − | 3394 |
|  | 1.0 | ND | − | 1938 |
|  | 0.1 | ND | − | 1630 |
| SEQ ID NO:6 | 100 | ND | − | 748 |
|  | 10 | ND | − | 3069 |
|  | 1.0 | ND | − | 1375 |
|  | 0.1 | ND | − | 1171 |
| SEQ ID NO:31 | 100 | 23 | +++ | 2039 |
|  | 10 | 24 | ++ | 200 |
|  | 1.0 | 25 | + | 901 |
|  | 0.1 | 26 | − | 1875 |
| Colostrinin | 10 | 20 | ++ | 2470 |
|  | 1.0 | 21 | + | 1614 |
|  | 0.1 | 22 | − | 2535 |
| Colostrum | 100 | 17 | ++ | 1094 |
|  | 10 | 18 | − | 2991 |
|  | 1.0 | 19 | − | 3320 |
|  | 0.1 | ND | − | 2717 |
| SEA | .02 | ND | ++++ | 6554 |
| Control |  | 27 | − | 461 |

ND = not done
+++ = strong induction of lymphoblasts and/or monocytes
++ = medium induction of lymphoblasts and/or monocytes
+ = low induction of lymphoblasts and/or monocytes
+/− = some induction of lymphoblasts and/or monocytes
− = same as control
Mitogenic Activity = CPM above control as determined by 24-hour $^3$H-thymidine incorporation.

Cytokine studies:

Colostrinin has previously been shown in the literature to induce IFN-γ and TNF-α, as has Val-Glu-Ser-Tyr-Val-Pro-Leu-Phe-Pro (SEQ ID NO:31), which is disclosed in International Publication No. WO-A-98/14473. Thus, studies were done to investigate the individual peptides.

Cytokine concentrations were also determined from cells following 72 hours of incubation with concentrations of colostrinin and its constituent peptides (CCP) ranging from 100 to 0.1 µg/ml, and colostrum and high- or low-iron baby formula (Enfamil) at various dilutions. Supernatant fluids were then subjected to enzyme-linked immunosorbent assay (ELISA) for the following commercially available cytokines: interferon-gamma (IFN-γ), tumor necrosis factor alpha (TNF-α), interleukin (IL)-4, IL-6, IL-10, and IL-12.

Table 2 represents the results of approximately 250 single assays. More specifically, in these studies it was found that many of the peptides including colostrinin induced IFN-γ and that the data corresponds with $^3$H-thymidine incorporation (Tables 1 and 3). Interestingly the maximum cytokine inducing activity of many of the peptides was not diluted out until the 1.0 or 0.1 μg/ml concentrations of peptide were used (Shaded numbers in Table 2), or in the case of IFN-γ and TNF-α induction by SEQ ID NO:31 and SEQ ID NO:1, 0.1 μg/ml rather than higher concentrations. This finding may be consistent with a phasic response like those of hormones or of toxicity present in higher concentrations.

The ability to induce IFN-γ by some of the peptides decayed over time. For example, SEQ ID NO:31 at 0.1 μg/ml at the beginning of the studies induced 324 pg IFN-γ/ml and in the last experiments induced no detectable levels. Although the peptides lost the IFN-γ inducing activity over a period of four months when stored in solution, some of the peptides were still able to induce TNF-α, IL-6, and IL-12, but the levels produced were somewhat lower than in the earlier studies. In contrast, induction of TNF-α and IL-10 by colostrinin and colostrum was still very high at this time. Thus, the complexed peptides making up colostrinin and colostrum may be more stable and/or combinations of peptides in colostrinin and colostrum may be more potent. Additional factors that may account for the variations of the peptides in these studies include: 1) natural variations in the immune state of the individuals donating the leukocytes, 2) the possibility that aggregation occurred in samples stored in PBS, thus reducing in effective number of molecules able to react, and 3) the possibility that the individual peptides may be subject to oxidative damage or some other inactivating process. The fact that the peptide, SEQ ID NO:8, which still induced IFN-γ in the last experiment (Example 3) was stored in 33% DMSO suggests an oxidative process or aggregation problem may be responsible for loss, or reduction of inducing activity in peptide samples stored in phosphate buffered saline (PBS). However, the samples in PBS appeared to be in solution at the time of the induction experiments.

TABLE 2

Cytokines induced in human leukocyte cultures stimulated with CCP, colostrum or commercial milk formulas.

| PEPTIDE (Exp. #) | PEPTIDE CONCENTRATION (mg/ml) | IFN γ (pg/ml) | TNF-α (pg/ml) | IL-10 (pg/ml) |
|---|---|---|---|---|
| Example 1 | | | | |
| SEQ ID NO:1 | 100 | 54 | 478 | 168 |
| | 10 | 528 | >1000 | 940 |
| | 1 | 584 | >1000 | 1070 |
| | 0.1 | 236 | 722 | 696 |
| SEQ ID NO:7 | 100 | 317 | >1000 | 998 |
| | 10 | 409 | >1000 | 1134 |
| SEQ ID NO:8 | 100 | 419 | >1000 | 860 |
| | 10 | 775 | >1000 | 1643 |
| | 1 | 877 | >1000 | 2223 |
| | 0.1 | 642 | >1000 | 1350 |
| SEQ ID NO:3 | 1 | 809 | >1000 | 1611 |
| | 0.1 | 206 | 802 | 611 |
| SEQ ID NO:2 | 100 | 372 | >1000 | 754 |
| | 10 | 410 | >1000 | 1063 |
| | 1 | 826 | >1000 | 2092 |
| | 0.1 | 259 | >1000 | 596 |
| SEQ ID NO:4 | 10 | 794 | >1000 | 1494 |
| | 1 | 723 | >1000 | 1765 |
| SEQ ID NO:5 | 100 | 559 | >1000 | 756 |
| | 10 | 626 | >1000 | 1158 |

TABLE 2-continued

Cytokines induced in human leukocyte cultures stimulated with CCP, colostrum or commercial milk formulas.

| PEPTIDE | CONC | IFN γ | TNF-α | IL-10 |
|---|---|---|---|---|
| SEQ ID NO:6 | 100 | 91 | 718 | 302 |
| | 10 | 621 | >1000 | 1203 |
| SEQ ID NO:31 | 100 | 371 | 804 | 4234 |
| | 10 | 107 | 379 | 1834 |
| | 1 | 118 | 651 | 242 |
| | 0.1 | 324 | >1000 | 356 |
| Colostrin | 10 | 888 | >1000 | 1515 |
| | 1 | 878 | >1000 | 1150 |
| | 0.1 | 156 | 760 | 451 |
| Raw Colostrum | 100 | 807 | >1000 | 857 |
| | 10 | 530 | >1000 | 1074 |
| | 1 | 934 | >1000 | 1645 |
| | 0.1 | 192 | 848 | 391 |
| Control | | 4 | 52 | 0 |
| SEA | | 902 | >1000 | 4676 |
| Example 2 | | | | |
| SEQ ID NO:18 | 100 | 4 | 24 | 36 |
| SEQ ID NO:19 | 10 | 6 | 65 | 76 |
| | 1 | 463 | >1000 | 502 |
| SEQ ID NO:20 | 100 | 9 | 30 | 21 |
| | 10 | 31 | 118 | 101 |
| SEQ ID NO:22 | 100 | 535 | >1000 | 524 |
| | 10 | 539 | 985 | 409 |
| | 1 | 649 | >1000 | 460 |
| | 0.1 | 147 | 636 | 207 |
| SEQ ID NO:1 | 100 | 9 | 92 | 108 |
| | 10 | 14 | 99 | 129 |
| | 1 | 287 | 728 | 292 |
| | 0.1 | 576 | >1000 | 397 |
| SEQ ID NO:7 | 100 | 262.9 | >1000 | 639 |
| SEQ ID NO:3 | 100 | 980 | >1000 | 646 |
| | 10 | 828 | >1000 | 651 |
| | 1 | 914 | >1000 | 1093 |
| | 0.1 | 281 | 685 | 348 |
| Enfamil Low Iron | 1:5 | 101 | 305 | 24 |
| | 1:10 | 167 | 406 | 443 |
| Enfamil with Iron | 1:5 | 24 | 528 | 136 |
| | 1:10 | 10 | 320 | 702 |
| Control | | 7 | 248 | 180 |
| SEA | | 901 | >1000 | 2806 |
| Example 3 | | | | |
| SEQ ID NO:1 | 100 | 6 | 110 | 0 |
| | 10 | 4 | ND | ND |
| SEQ ID NO:7 | 1 | 9 | 57 | 0 |
| | 0.1 | 6 | ND | ND |
| SEQ ID NO:8 | 10 | 8 | 26 | 0 |
| | 1 | 288 | ND | ND |
| SEQ ID NO:3 | 100 | 3 | 0 | 0 |
| Raw Colostrum | 100 | 5 | 11 | 0 |
| | 10 | 15 | 520 | 569 |
| | 1 | 0 | ND | ND |
| | 0.1 | 0 | ND | ND |
| Colostrinin | 10 | 0 | >1000 | 3662 |
| | 1 | 18 | 910 | 1839 |
| | 0.1 | 1 | ND | ND |
| SEQ ID NO:31 | 10 | 0 | 11 | 0 |
| | 1 | 0 | 90 | 0 |
| | 0.1 | 0 | ND | ND |
| SEQ ID NO:22 | 100 | 0 | 120 | 77.6 |
| | 10 | 0 | 60 | 0 |
| | 1 | 0 | 7 | 0 |
| | 0.1 | 0 | ND | ND |
| Enfamil Low Iron | 1:5 | 25 | 339 | 51 |
| Enfamil with Iron | 1:5 | 0 | 452 | 51 |
| Control | | 0 | 0 | 0 |
| SEA | | 700 | >1000 | 2971 |

TABLE 2-continued

Cytokines induced in human leukocyte cultures stimulated with CCP, colostrum or commercial milk formulas.

Example 4

| | | | | |
|---|---|---|---|---|
| SEQ ID NO:1 | 100 | 0 | 73.3 | 0 |
| SEQ ID NO:2 | 1 | 0 | 0 | 0 |
| Colostrinin | 10 | 0 | 1790 | 6.9 |
| | 1 | 0 | 1813 | 0 |
| | 0.1 | ND | ND | ND |
| Raw Colostrum | 100 | 0 | 1834 | 4.0 |
| | 10 | 0 | 31.2 | 0 |
| | 1 | ND | ND | ND |
| Control | | 0 | 28.4 | 0 |
| SEA | | 3.5 | 1927 | 13.4 |

| PEPTIDE (Exp. #) | PEPTIDE CONCEN-TRATION (µg/ml) | IL-4 (pg/ml) | IL-6 (pg/ml) | IL-12 (pg/ml) |
|---|---|---|---|---|

Example 1

| | | | | |
|---|---|---|---|---|
| SEQ ID NO:1 | 100 | 0 | 235.4 | 0 |
| | 10 | 0 | 934.8 | 0 |
| | 1 | 0 | 675.3 | 0 |
| | 0.1 | 0 | 497.1 | 0 |
| SEQ ID NO:7 | 100 | 0 | 291.3 | 0 |
| | 10 | 0 | 645.4 | 0 |
| SEQ ID NO:8 | 100 | 0 | 1076 | 0 |
| | 10 | 0 | 1024 | 0 |
| | 1 | 0 | 1013 | 0 |
| | 0.1 | 0 | 533.6 | 0 |
| SEQ ID NO:3 | 1 | 0 | 620.5 | 0 |
| | 0.1 | 0 | 187 | 0 |
| SEQ ID NO:2 | 100 | 0 | 258.6 | 0 |
| | 10 | 0 | 551.3 | 0 |
| | 1 | 0 | 1205 | 0 |
| | 0.1 | 0 | 325 | 0 |
| SEQ ID NO:4 | 10 | 0 | 1718 | 0 |
| | 1 | 0 | 744.4 | 0 |
| SEQ ID NO:5 | 100 | 0 | 98.2 | 0 |
| | 10 | 0 | 750 | 0 |
| SEQ ID NO:6 | 100 | 0 | 63.3 | 0 |
| | 10 | 0 | 864.5 | 0 |
| SEQ ID NO:31 | 100 | 1.4 | 1489 | 0 |
| | 10 | 0 | 836.3 | 0 |
| | 1 | 0.4 | 489.9 | 0 |
| | 0.1 | 2.4 | 1635 | 0 |
| Colistrinin | 10 | 0 | 1832 | 0 |
| | 1 | 1.9 | 1915 | 0 |
| | 0.1 | 0.4 | 430.1 | 0 |
| Raw Colostrum | 100 | 0 | 1679 | 0 |
| | 10 | 0 | 602.2 | 0 |
| | 1 | 0 | 1055 | 0 |
| | 0.1 | 5.0 | 187.2 | 0 |
| Control | | 0 | 13.5 | 0 |
| SEA | | 4 | 1704 | 0 |

Example 2

| | | | | |
|---|---|---|---|---|
| SEQ ID NO:18 | 100 | 0 | | 0 |
| SEQ ID NO:19 | 10 | 0 | | 0 |
| | 1 | 33.8 | | 0 |
| SEQ ID NO:20 | 100 | 0 | | 0 |
| | 10 | 0.4 | | 0 |
| SEQ ID NO:22 | 100 | 41.5 | | 0 |
| | 10 | 32.7 | | 0 |
| | 1 | 30.1 | | 0 |
| | 0.1 | 17.8 | | 0 |
| SEQ ID NO:3 | 100 | 0 | | 0 |
| | 10 | 3.5 | | 5.7 |
| | 1 | 26.6 | | 0 |
| | 0.1 | 47.6 | | 0 |
| SEQ ID NO:7 | 100 | 24.5 | | 0 |
| SEQ ID NO:2 | 100 | 22.5 | | 33.5 |
| | 10 | 19.9 | | 0 |
| | 1 | 10.1 | | 9.9 |
| | 0.1 | 29.1 | | 2.2 |
| Enfamil Low Iron | 1:5 | 0.9 | | 0 |
| | 1:10 | 4.0 | | 0 |
| Enfamil with Iron | 1:5 | 0 | | 0 |
| | 1:10 | 0 | | 0 |
| Control | | 0 | | 0 |
| SEA | | 62.5 | | 54.8 |

Example 3

| | | | | |
|---|---|---|---|---|
| SEQ ID NO:1 | 100 | 0 | 942.5 | 0 |
| | 10 | ND | ND | ND |
| SEQ ID NO:7 | 1 | 0 | 32.9 | 0 |
| | 0.1 | ND | ND | ND |
| SEQ ID NO:8 | 10 | 0 | 18.5 | 4.0 |
| | 1 | ND | ND | ND |
| SEQ ID NO:5 | 100 | 0 | 0 | 0 |
| Raw Colostrum | 100 | 0 | 0 | 0 |
| | 10 | 0 | 1853 | 1.6 |
| | 1 | ND | ND | ND |
| | 0.1 | ND | ND | ND |
| Colostrinin | 10 | 0 | 2009 | 17.6 |
| | 1 | 0 | 1861 | 7.5 |
| | 0.1 | ND | ND | ND |
| SEQ ID NO:31 | 10 | 0 | 16.8 | 18.7 |
| | 1 | 0 | 722.9 | 0 |
| | 0.1 | ND | ND | ND |
| SEQ ID NO:22 | 100 | 6.0 | 1630 | 0 |
| | 10 | 0 | 46.7 | 0 |
| | 1 | 0 | 0 | 0 |
| | 0.1 | ND | ND | ND |
| Enfamil Low Iron | 1:5 | 0 | 1913 | 0 |
| Enfamil with Iron | 1:5 | 0.4 | 1953 | 0 |
| Control | | 0 | 0 | 0 |
| SEA | | 16.8 | 866.2 | 0 |

*SEQ ID NOs:1-8 and 31, Raw Colostrum, and Colostrinin were reconstituted on the same day.
*SEQ ID NOs:18, 19, 20, and 22 were reconstituted on the same day.

The relative abilities of the various peptides to induce cytokines are shown in Table 3. The peptides were ranked according to their abilities to induce the indicated cytokine by first comparing the raw numbers at the 0.1 µg/ml concentration followed by 1.0 µg/ml concentrations and then higher concentrations, i.e., 10 and 100 µg/ml. It can be noted that SEQ ID NOs:1, 8, 3, 2, and 31 were the best overall inducers in almost all cytokine and blood cell proliferation experiments. Peptides SEQ ID NOs:7, 4, and 5 were generally less effective as inducers. Colistrinin and colostrum ranked generally in the middle, however, only 1:5 and 1:10 dilutions of colostrum were used, thus actual comparison are not accurate since specific proteins present and their concentrations were not determined for colostrum. It is important to note, however, that colostrum contained substances that could induce cytokines in a similar fashion to colostrinin and its component peptides.

When the colostrinin constituent peptides having a β-casein precursor (SEQ ID NOs: 18, 19, 20, and 22) were compared to the initially tested SEQ ID NOs:1-8 and 31, the latter were better inducers. SEQ ID NO:22 was generally the best inducer of those peptides having a β-casein precursor. It was also found that Enfamil low iron baby formula induced higher levels of cytokines than the Enfamil high iron formula.

TABLE 3

Relative abilities of the various peptides to induce cytokines and proliferation

| Rank | Ex. 1 IFN-γ | Ex. 2 IFN-γ | Ex. 1 Micro. Resp. | Ex. 1 Prolif. Resp. | Ex. 1 TNF-α | Ex. 2 TNF-α | Ex. 1 IL-10 |
|---|---|---|---|---|---|---|---|
| 1 | SEQ ID NO:8 | SEQ ID NO:1 | SEQ ID NO:8 | SEQ ID NO:2 | SEQ ID NO:2** | SEQ ID NO:2 | SEQ ID NO:8 |
| 2 | SEQ ID NO:31 | SEQ ID NO:2 | SEQ ID NO:2 | SEQ ID NO:1 | SEQ ID NO:8 | SEQ ID NO:1 | SEQ ID NO:1 |
| 3 | SEQ ID NO:2 | SEQ ID NO:7 | SEQ ID NO:31 | SEQ ID NO:4 | SEQ ID NO:31 | SEQ ID NO:7 | SEQ ID NO:3 |
| 4 | SEQ ID NO:1 | SEQ ID NO:22 | SEQ ID NO:1 | Colostrum | Colostrum | SEQ ID NO:22 | SEQ ID NO:2 |
| 5 | SEQ ID NO:3 | SEQ ID NO:19 | SEQ ID NO:7 | Colostrinin | Colostrinin | SEQ ID NO:19 | Colostrinin |
| 6 | Colostrinin | SEQ ID NO:20 | Colostrinin | SEQ ID NO:8 | SEQ ID NO:3 | SEQ ID NO:20 | Colostrum |
| 7 | Colostrum | SEQ ID NO:18 | Colostrum | SEQ ID NO:31 | SEQ ID NO:1 | SEQ ID NO:18 | SEQ ID NO:31 |
| 8 | SEQ ID NO:4 | | SEQ ID NO:3 | SEQ ID NO:5 | SEQ ID NO:5 | | SEQ ID NO:4 |
| 9 | SEQ ID NO:5 | | SEQ ID NO:4 | SEQ ID NO:6 | SEQ ID NO:7 | Low Enfamil | SEQ ID NO:7 |
| 9 | SEQ ID NO:6 | | SEQ ID NO:5 | SEQ ID NO:7 | SEQ ID NO:4 | High Enfamil | SEQ ID NO:5 |
| 10 | SEQ ID NO:7 | | SEQ ID NO:6 | SEQ ID NO:3 | SEQ ID NO:6 | | SEQ ID NO:6 |

| Rank | Ex. 2 IL-10 | Ex. 1 IL-4 | Ex. 2 IL-4 | Ex. 1 IL-6 | Ex. 1 IL-12 | Ex. 2 IL-12 |
|---|---|---|---|---|---|---|
| 1 | SEQ ID NO:2 | Colostrum | SEQ ID NO:1 | SEQ ID NO:31 | All neg. | SEQ ID NO:2 |
| 2 | SEQ ID NO:7 | Colostrinin | SEQ ID NO:2 | SEQ ID NO:8 | | SEQ ID NO:1 |
| 3 | SEQ ID NO:1 | SEQ ID NO:31 | SEQ ID NO:22 | SEQ ID NO:1 | | |
| 4 | SEQ ID NO:19 | | SEQ ID NO:19 | Colostrinin | | |
| 5 | SEQ ID NO:22 | | SEQ ID NO:7 | SEQ ID NO:2 | | |
| 6 | SEQ ID NO:20 | | Low Enfamil | Colostrum | | |
| 7 | SEQ ID NO:18 | | | SEQ ID NO:3 | | |
| 8 | | | | SEQ ID NO:4 | | |
| 9 | Low Enfamil | | | SEQ ID NO:6 | | |
| 9 | High Enfamil | | | SEQ ID NO:5 | | |
| 10 | | | | SEQ ID NO:7 | | |

*SEQ ID NO:7 <2 fold difference in titer
**All good inducers
***No difference in titer Although the invention has been disclosed with reference to its preferred embodiments, from reading this description those of skill in the art may appreciate changes and modification that may be made which do not depart from the scope and spirit of the invention as described above and claimed hereafter. All references, patents, and patent applications cited herein are incorporated herein by reference in their entirety as if individually incorporated.

Sequence Listing Free Text

The following are all synthetic peptide sequences.

| | |
|---|---|
| SEQ ID NO:1 | MQPPPLP |
| SEQ ID NO:2 | LQTPQPLLQVMMEFQGD |
| SEQ ID NO:3 | DQPPDVEKPDLQPFQVQS |
| SEQ ID NO:4 | LFFFLPVVNVLP |
| SEQ ID NO:5 | DLEMPVLPVEPFPFV |
| SEQ ID NO:6 | MPQNFYKLPQM |
| SEQ ID NO:7 | VLEMKFPPFPQETVT |
| SEQ ID NO:8 | LKPFPKLKVEVFPFP |
| SEQ ID NO:9 | VVMEV |
| SEQ ID NO:10 | SEQP |
| SEQ ID NO:11 | DKE |
| SEQ ID NO:12 | FPPFK |
| SEQ ID NO:13 | DSQPPV |
| SEQ ID NO:14 | DPPPPQS |
| SEQ ID NO:15 | SEEMP |
| SEQ ID NO:16 | KYKLQPE |
| SEQ ID NO:17 | VLPPNVG |

| | |
|---|---|
| SEQ ID NO:18 | VYPFTGPIPN |
| SEQ ID NO:19 | SLPQNILPL |
| SEQ ID NO:20 | TQTPVVVPPF |
| SEQ ID NO:21 | LQPEIMGVPKVKETMVPK |
| SEQ ID NO:22 | HKEMPFPKYPVEPFTESQ |
| SEQ ID NO:23 | SLTLTDVEKLHLPLPLVQ |
| SEQ ID NO:24 | SWMHQPF |
| SEQ ID NO:25 | QPLPPTVMFP |
| SEQ ID NO:26 | PQSVLS |

| | |
|---|---|
| SEQ ID NO:27 | LSQPKVLPVPQKAVPQRDMPIQ |
| SEQ ID NO:28 | AFLLYQE |
| SEQ ID NO:29 | RGPFPILV |
| SEQ ID NO:30 | AIFNRYQDDHGEEILKSL |
| SEQ ID NO:31 | VESYVPLFP |
| SEQ ID NO:32 | FLLYQEPVLGPVR |
| SEQ ID NO:33 | LNF |
| SEQ ID NO:34 | MHQPFQPLPPTVMFP |

SEQUENCE LISTING

<160> NUMBER OF SEQ ID NOS: 34

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: synthetic peptide

<400> SEQUENCE: 1

Met Gln Pro Pro Pro Leu Pro
 1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: synthetic peptide

<400> SEQUENCE: 2

Leu Gln Thr Pro Gln Pro Leu Leu Gln Val Met Met Glu Pro Gln Gly
 1               5                  10                  15
Asp

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: synthetic peptide

<400> SEQUENCE: 3

Asp Gln Pro Pro Asp Val Glu Lys Pro Asp Leu Gln Pro Phe Gln Val
 1               5                  10                  15
Gln Ser

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthetic peptide

<400> SEQUENCE: 4

Leu Phe Phe Phe Leu Pro Val Val Asn Val Leu Pro
 1               5                  10

-continued

```
<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Asp Leu Glu Met Pro Val Leu Pro Val Glu Pro Phe Pro Phe Val
 1               5                  10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Met Pro Gln Asn Phe Tyr Lys Leu Pro Gln Met
 1               5                  10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Val Leu Glu Met Lys Phe Pro Pro Pro Gln Glu Thr Val Thr
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Leu Lys Pro Phe Pro Lys Leu Lys Val Glu Val Phe Pro Phe Pro
 1               5                  10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Val Val Met Glu Val
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 10

Ser Glu Gln Pro
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Asp Lys Glu
 1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Phe Pro Pro Pro Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Asp Ser Gln Pro Pro Val
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Asp Pro Pro Pro Pro Gln Ser
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Ser Glu Glu Met Pro
 1               5

<210> SEQ ID NO 16
<211> LENGTH: 7
<212> TYPE: PRT
```

-continued

```
<213> ORGANISM: Artificial Sequence
<220> FEATURE:
<223> OTHER INFORMATION: Description of Artificial Sequence: synthetic
      peptide

<400> SEQUENCE: 16

Lys Tyr Lys Leu Gln Pro Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Val Leu Pro Pro Asn Val Gly
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Val Tyr Pro Phe Thr Gly Pro Ile Pro Asn
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

Ser Leu Pro Gln Asn Ile Leu Pro Leu
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 20

Thr Gln Thr Pro Val Val Val Pro Pro Phe
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Leu Gln Pro Glu Ile Met Gly Val Pro Lys Val Lys Glu Thr Met Val
1               5                   10                  15
```

-continued

Pro Lys

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

His Lys Glu Met Pro Phe Pro Lys Tyr Pro Val Glu Pro Phe Thr Glu
 1               5                  10                  15

Ser Gln

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Ser Leu Thr Leu Thr Asp Val Glu Lys Leu His Leu Pro Leu Pro Leu
 1               5                  10                  15

Val Gln

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Ser Trp Met His Gln Pro Pro
 1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Gln Pro Leu Pro Pro Thr Val Met Phe Pro
 1               5                  10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

Pro Gln Ser Val Leu Ser
 1               5

<210> SEQ ID NO 27

```
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 27

Leu Ser Gln Pro Lys Val Leu Pro Val Pro Gln Lys Ala Val Pro Gln
1               5                   10                  15

Arg Asp Met Pro Ile Gln
            20

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 28

Ala Phe Leu Leu Tyr Gln Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 29

Arg Gly Pro Phe Pro Ile Leu Val
1               5

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 30

Ala Thr Phe Asn Arg Tyr Gln Asp Asp His Gly Glu Glu Ile Leu Lys
1               5                   10                  15

Ser Leu

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 31

Val Glu Ser Tyr Val Pro Leu Phe Pro
1               5

<210> SEQ ID NO 32
<211> LENGTH: 13
<212> TYPE: PRT
<213> ORGANISM: Artificial Sequence
<220> FEATURE:
```

```
<223> OTHER INFORMATION: Description of Artificial Sequence: synthetic
      peptide

<400> SEQUENCE: 32

Phe Leu Leu Tyr Gln Glu Pro Val Leu Gly Pro Val Arg
 1               5                   10

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 33

Leu Asn Phe
 1

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 34

Met His Gln Pro Pro Gln Pro Leu Pro Pro Thr Val Met Phe Pro
 1               5                   10                  15
```

We claim:

1. A method for inducing a cytokine in a cell, the method comprising contacting the cell with an immunological regulator under conditions effective to induce a cytokine, wherein the immunological regulator is selected from the group consisting of a constituent peptide of colostrinin, an active analog thereof, and combinations thereof;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34); and wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34) and wherein said active analog induces a cytokine.

2. The method of claim 1 wherein the cell is present in a cell culture, a tissue, an organ, or an organism.

3. The method of claim 1 wherein the cell is a mammalian cell.

4. The method of claim 3 wherein the cell is a human cell.

5. The method of claim 1 wherein the immunological regulator is the colostrinin constituent peptide MQPPPLP (SEQ ID NO: 1), an active analog thereof, or a combination thereof.

6. A method for modulating an immune response in a cell, the method comprising contacting the cell with an immunological regulator under conditions effective to induce a cytokine, wherein the immunological regulator is selected from the group consisting of a constituent peptide of colostrinin, an active analog thereof, and combinations thereof;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34); and wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34) and wherein said active analog modulates an immune response.

7. The method of claim 6 wherein the cell is present in a cell culture, a tissue, an organ, or an organism.

8. The method of claim 6 wherein the cell is a mammalian cell.

9. The method of claim 8 wherein the cell is a human cell.

10. The method of claim 6 wherein the immunological regulator is the colostrinin constituent peptide MQPPPLP (SEQ ID NO: 1), an active analog thereof, or a combination thereof.

11. A method for modulating an immune response in a patient, the method comprising administering to the patient an immunological regulator under conditions effective to induce a cytokine, wherein the immunological regulator is selected from the group consisting of a constituent peptide of colostrinin, an active analog thereof, and combinations thereof;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34); and wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), and MHQPPQPLPPTVMFP (SEQ ID NO:34) and wherein said active analog modulates an immune response.

12. The method of claim 11 wherein the immunological regulator is administered as part of a dietary supplement.

13. The method of claim 11 wherein the immunological regulator is administered topically.

14. The method of claim 11 wherein the patient is an animal.

15. The method of claim 14 wherein the patient is a human.

16. The method of claim 11 wherein the immune response is a specific immune response.

17. The method of claim 11 wherein the immune response is a nonspecific immune response.

18. The method of claim 11 wherein the immune response is the interferon response or antibody production.

19. The method of claim 11 wherein the immunological regulator is the colostrinin constituent peptide MQPPPLP (SEQ ID NO: 1), an active analog thereof, or a combination thereof.

20. A method for modulating leukocyte proliferation, the method comprising contacting leukocytes with a leukocyte regulator selected from the group consisting of colostrinin, a constituent peptide thereof, an active analog thereof, and combinations thereof, under conditions effective to change the number of leukocytes, wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34);

wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34);

and wherein the number of leukocytes is changed.

21. The method of claim 20 wherein the leukocytes are present in a cell culture or an organism.

22. The method of claim 20 wherein the leukocytes are mammalian cells.

23. The method of claim 22 wherein the leukocytes are human cells.

24. The method of claim 20 wherein the leukocytes are increased in number.

25. The method of claim 24 wherein the leukocytes are differentiated.

26. The method of claim 20 wherein the leukocyte regulator is a constituent peptide of colostrinin.

27. The method of claim 20 wherein the leukocyte regulator is the colostrinin constituent peptide VESYVPLFP (SEQ ID NO:31), an active analog thereof, or a combination thereof.

28. The method of claim 20 wherein the leukocyte regulator is the colostrinin constituent peptide MQPPPLP (SEQ ID NO:1), an active analog thereof, or a combination thereof.

29. A method for modulating leukocyte proliferation in a patient, the method comprising administering to the patient a leukocyte regulator selected from the group consisting of colostrinin, a constituent peptide thereof, an active analog thereof, and combinations thereof, under conditions effective to change the number of leukocytes;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34);

wherein the active analog comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34), and wherein the number of leukocytes is changed.

30. The method of claim 29 wherein the patient is a human.

31. The method of claim 29 wherein the leukocytes are increased in number.

32. The method of claim 31 wherein the leukocytes are differentiated.

33. The method of claim 29 wherein the leukocyte regulator is a constituent peptide of colostrinin.

34. The method of claim 29 wherein the leukocyte regulator is the colostrinin constituent peptide VESYVPLFP (SEQ ID NO:31), an active analog thereof, or a combination thereof.

35. The method of claim 29 wherein the leukocyte regulator is the colostrinin constituent peptide MQPPPLP (SEQ ID NO:1), an active analog thereof, or a combination thereof.

36. The method of claim 29 wherein the leukocyte regulator is administered as part of a dietary supplement.

37. The method of claim 29 wherein the leukocyte regulator is administered topically.

* * * * *

UNITED STATES PATENT AND TRADEMARK OFFICE
CERTIFICATE OF CORRECTION

PATENT NO. : 6,903,068 B1
APPLICATION NO. : 09/641801
DATED : June 7, 2005
INVENTOR(S) : Stanton et al.

Page 1 of 1

It is certified that error appears in the above-identified patent and that said Letters Patent is hereby corrected as shown below:

Column 32, line 61, Claim 1, delete "SEQ ID KO:3" and insert --SEQ ID NO:3--;

Column 33, line 5, Claim 1, delete "SEQ ID KO:3" and insert --SEQ ID NO:3--;

Column 33, line 31, Claim 6, delete "SEQ ID KO:3" and insert --SEQ ID NO:3--;

Column 33, line 42, Claim 6, delete "SEQ ID KO:3" and insert --SEQ ID NO:3--;

Column 34, line 1, Claim 11, delete "SEQ ID KO:3" and insert --SEQ ID NO:3--;

Column 34, line 13, Claim 11, delete "SEQ ID KO:3" and insert --SEQ ID NO:3--;

Column 34, line 47, Claim 20, delete "SEQ ID KO:3" and insert --SEQ ID NO:3--;

Column 34, line 60, Claim 20, delete "SEQ ID KO:3" and insert --SEQ ID NO:3--;

Column 35, line 30, Claim 29, delete "SEQ ID KO:3" and insert --SEQ ID NO:3--;

Column 36, line 7, Claim 29, delete "SEQ ID KO:3" and insert --SEQ ID NO:3--;

Signed and Sealed this

Thirty-first Day of March, 2009

JOHN DOLL
*Acting Director of the United States Patent and Trademark Office*